United States Patent
Zhang et al.

(10) Patent No.: US 10,322,132 B2
(45) Date of Patent: Jun. 18, 2019

(54) PREVENTION OR TREATMENT OF URATIC OR GOUTY DISEASES

(71) Applicant: SHANTON PHARMA CO., LTD., Shanghai (CN)

(72) Inventors: Qian Zhang, Jinan (CN); Zhenhua Huang, Jinan (CN); Jinrong Liu, Jinan (CN); Shuangshuang Chi, Jinan (CN)

(73) Assignee: SHANTON PHARMA CO., LTD, Shanghai (CN)

( * ) Notice: Subject to any disclaimer, the term of this patent is extended or adjusted under 35 U.S.C. 154(b) by 0 days.

(21) Appl. No.: 15/512,412

(22) PCT Filed: Jan. 28, 2016

(86) PCT No.: PCT/CN2016/000061
§ 371 (c)(1),
(2) Date: Mar. 17, 2017

(87) PCT Pub. No.: WO2016/119570
PCT Pub. Date: Aug. 4, 2016

(65) Prior Publication Data
US 2017/0326148 A1 Nov. 16, 2017

(30) Foreign Application Priority Data

| Jan. 30, 2015 | (CN) | 2015 1 0048096 |
| Feb. 13, 2015 | (CN) | 2015 1 0079809 |
| Feb. 13, 2015 | (CN) | 2015 1 0080714 |
| Apr. 30, 2015 | (CN) | 2015 1 0216089 |

(51) Int. Cl.
| *A61K 31/522* | (2006.01) |
| *C07D 473/06* | (2006.01) |
| *C07D 473/08* | (2006.01) |
| *A61K 31/4188* | (2006.01) |
| *C07D 473/04* | (2006.01) |
| *C07D 487/04* | (2006.01) |

(52) U.S. Cl.
CPC ........ *A61K 31/522* (2013.01); *A61K 31/4188* (2013.01); *C07D 473/04* (2013.01); *C07D 473/06* (2013.01); *C07D 473/08* (2013.01); *C07D 487/04* (2013.01); *A61K 2300/00* (2013.01)

(58) Field of Classification Search
CPC .............. A61K 31/522; A61K 31/4188; C07D 487/04; C07D 473/04; C07D 473/08; C07D 473/06
See application file for complete search history.

(56) References Cited

U.S. PATENT DOCUMENTS

| 2007/0135456 A1 | 6/2007 | Pinto et al. |
| 2011/0136835 A1 | 6/2011 | Kitt et al. |
| 2013/0150383 A1 | 6/2013 | Pinto et al. |
| 2015/0080418 A1 | 3/2015 | Pinto et al. |

FOREIGN PATENT DOCUMENTS

| CN | 101103030 A | * 1/2008 | ........... C07D 473/04 |
| CN | 101103030 A | 1/2008 | |
| CN | 101479273 A | 7/2009 | |
| EP | 0389282 | 9/1990 | |
| WO | 9316699 | 9/1993 | |
| WO | 9920280 | 4/1999 | |
| WO | 2005077950 | 8/2005 | |
| WO | 2010/071865 A1 | 6/2010 | |
| WO | 2011057110 | 5/2011 | |

OTHER PUBLICATIONS

International Patent Application No. PCT/CN2016/000061, "International Search Report" dated Aug. 4, 2016.
Chai et al., GPR109A and Vascular Inflammation, Curr Atheroscler Rep., vol. 15, No. 325, 2013, pp. 1-10.
Gaillard et al., Design and Synthesis of the First Generation of Novel Potent, Selective, and in Vivo Active (Benzothiazol-2-yl)acetonitrile Inhibitors of the c-Jun N-Terminal, J. Med. Chem., vol. 48, No. 14, 2005, pp. 4596-4607.
Komoriya et al., Hypouricemic effect of allopurinol and the novel xanthine oxidase inhibitor TEI-6720 in chimpanzees, Eur J Pharmacol., vol. 250, No. 3, 1993, pp. 455-460.

(Continued)

*Primary Examiner* — Emily A Bernhardt
*Assistant Examiner* — Laura M Daniel
(74) *Attorney, Agent, or Firm* — Kilpatrick Townsend & Stockton LLP

(57) ABSTRACT

The present invention relates to the use of a compound of formula (I), a pharmaceutically acceptable salt thereof, a solvate thereof, or a pharmaceutical composition containing the same in reducing uric acid level, preventing or reducing inflammations, and preventing or treating uratic or gouty diseases. In particular, the present invention relates to the use of a compound of formula (I), a pharmaceutically acceptable salt thereof, a solvate thereof, or a pharmaceutical composition containing the same in the manufacture of a medicament for the treatment or prevention of hyperuricemia, gout, gouty inflammations, pain and uric acid nephropathy.

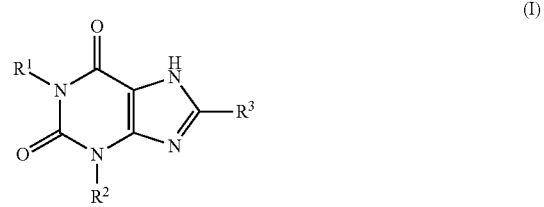

(I)

$R^1$ represents hydrogen, $C_{1-4}$ alkyl or the like. $R^2$ represents $C_{1-10}$ alkyl or the like.
$R^3$ represents halogen or the like.

20 Claims, No Drawings

(56) References Cited

OTHER PUBLICATIONS

Lee et al., Soft Coral-Derived Lemnalol Alleviates Monosodium Urate-Induced Gouty Arthritis in Rats by Inhibiting Leukocyte Infiltration and iNOS, COX-2 and c-Fos Protein Expression, Mar. Drugs, vol. 11, www.mdpi.com/journal/marinedrugs, 2013, pp. 99-113.
Sass et al., Cytokine Expression in Three Mouse Models of Experimental Hepatitis, Cytokine, vol. 19, No. 3, Aug. 7, 2002, pp. 115-120.
Shen et al., Novel patent publications on high-affinity nicotinic acid receptor agonists, Expert Opin. Ther. Patents, vol. 19, No. 7, 2009, pp. 957-967.
Soond et al., PI3K p110δ regulates T-cell cytokine production during primary and secondary immune responses in mice and humans, Blood, vol. 115, No. 11, Mar. 18, 2010, pp. 2203-2213.
Terkeltaub et al., The interleukin 1 inhibitor rilonacept in treatment of chronic gouty arthritis: results of a placebo-controlled, monosequence crossover, non-randomised, single-blind pilot study, Ann Rheum Dis, vol. 68, 2009, pp. 1613-1617.
Wakade et al., Upregulation of GPR109A in Parkinson's Disease, PLoS One, vol. 9, No. 10, e109818, Oct. 17, 2014, pp. 1-10.
Canadian Application No. CA2,973,746, Office Action, dated Jul. 9, 2018, 6 pages.
European Application No. EP16742632.9, European Search Report, dated May 24, 2018, 7 pages.
Office Action issued in Israeli Application No. 253726 dated Oct. 17, 2018, along with an English translation.
Xin Yawen et al., "Advance in research of gout and its therapeutic drugs", Chinese Journal of medicinal Chemistry, vol.22 No. 5, pp. 416-423, Oct. 2012, along with an English abstract.
Russ Hile et al., "The inhibition of xanthine oxidase by 8-bromoxanthine", Journal of Biological Chemistry 259, No. 3, (1984), pp. 1570-1576.

* cited by examiner

PREVENTION OR TREATMENT OF URATIC OR GOUTY DISEASES

CROSS-REFERENCE TO RELATED APPLICATIONS

This application is a national stage application under 35 U.S.C. § 371 of PCT/CN2016/000061, filed Jan. 28, 2016, which claims priority to Chinese Application Nos.: 201510048096.3, filed Jan. 30, 2015; 201510079809.2, filed Feb. 13, 2015; 201510080714.2, filed Feb. 13, 2015; and 201510216089.X, filed Apr. 30, 2015, the disclosures of each of which are hereby incorporated by reference herein in their entireties.

TECHNICAL FIELD

The present invention relates to the prevention or treatment of uratic or gouty diseases, more specifically, to compounds or compositions for the treatment or prevention of uratic or gouty diseases. The present invention also relates to methods for the treatment or prevention of uratic or gouty diseases, as well as to the use of said compounds or compositions for reducing the level of uric acid in a patient in need thereof, and for preventing or reducing inflammation, and their use for preparing therapeutic or prophylactic agents for uratic or gouty diseases.

BACKGROUND ART

High level of uric acid, or hyperuricemia is a metabolic disease caused by the increased level of uric acid in blood resulting from metabolic disorder of a substance in human body called purine. The production and excretion of uric acid in vivo are approximately in equal amounts. As to the production amount, one third is derived from foods, while two thirds is self-synthesized in vivo. As to the excretion pathway, one third is excreted by the intestinal tracts, while two thirds is excreted from the kidney. The level of uric acid will increase so long as any of the pathways mentioned above goes wrong. The increase in the level of uric acid will impede the secretion process of uric acid in blood so that uric acid could not be excreted. If the level of uric acid is too high, some other diseases may occur, such as gout, nephropathy and cardiovascular diseases.

High level of uric acid would cause gout. Gout is a kind of arthritis with recurrent episodes which results from the increased level of blood uric acid due to metabolic disorder of purine in human body. High level of uric acid would also cause gouty nephropathy, which is the kidney damage caused by hyperuricemia due to the excessive generation of blood uric acid without proper excretion. Patients having the severe hyperuricemia would have renal failure. Gout is a group of heterogeneous conditions with tissue injuries caused by the increase of blood uric acid. It is caused by metabolic disorder of purine in vivo and/or reduced excretion of uric acid, and exhibits episodes of hyperuricemia. The uric acid content in plasma of healthy people is 20-60 mg/L. When it exceeds 80 mg/L, urate crystals will be deposited at parts of human body like joints, soft tissues and kidney, and the resulting crystal precipitation will lead to arthritis, lithangiuria and kidney diseases, namely, "gout". Upon acute onset, urate microcrystals are deposited at joints, thus causing local granulocyte infiltration s and inflammatory responses. Upon recurrent onsets, joint deformity occurs with "tophi" formed. Gout has been a common disease in western countries and Japan for a long time. In recent years, gout has also become an epidemic in China (particularly in coastal regions).

The existing researches suggest that the acute onset of gout is an acute inflammatory process induced by urate crystals, which starts with the interactions between urate crystals and resident monocytes/macrophages, and finally spontaneously alleviates with several underlying mechanisms through a series of inflammatory responses. In most patients, the gout outbreak is related with the changing (increasing or decreasing) rate of blood uric acid level, yet irrelevant to the stable level of blood uric acid. The abrupt change of the blood uric acid level may bring changes in volume or shape to the crystals so that the crystals may move in tissue matrices, which would promote the release of urate crystals from the body parts where the formed tophi are deposited. It is the released microcrystals or the crystals newly formed locally that cause the inflammatory responses. The interactions between monocytes/macrophages and urate crystals are the key step to initiate the onset of acute gout. The interactions between urate crystals and resident macrophages initiate inflammatory responses and induce the infiltration of neutrophil granulocytes and monocytes to enhance inflammatory responses.

The onset of acute gout involves a number of inflammatory factors which mainly include chemokines such as IL-1β, IL-6, IL-18, TNF-α and IL-8 (CXCL-8). By determining the levels of inflammatory factors and anti-inflammatory factors in the joint fluids of patients at different stages of acute gout, it is found that at the early and middle stages of inflammation, there are the significant increases in the levels of inflammatory factors such as IL-1β, IL-6 and TNF-α and in the level of leukocytes within joint fluids.

At present, IL-1 is also known as lymphocyte stimulator, and is mainly produced by the activated monocyte-macrophage. The IL-1 has two different molecular forms, IL-1α and IL-1β. IL-1α and IL-1β synergistically stimulates the activation of antigen-presenting cells and T-cells and promotes proliferation of B cells and secretion of antibodies at low local concentrations, providing immune modulation. The precursor of IL-1β is produced by immune cells such as monocyte-macrophages and dendritic cells, and is converted to the activated IL-1β by Caspase-1 within NALP3 inflammasome complex. The activated IL-1β is released to mediate the inflammatory responses. IL-1β could trigger the release of IL-6 and IL-8 and mediate the infiltration of neutrophil granulocytes. Besides, the rapid clinical responses of acute gout patients against various IL-1 inhibitors also demonstrate the critical role of this factor in gout inflammations. The recent research data show that interleukin 1β (IL1β) plays an important role in the inflammation process caused by the deposition of sodium urate (MSU) crystals in gout patients (Ann Rheum Dis 2009; 68: 1613-1617).

TNF-α (tumor necrosis factor) is a polypeptide-typed cytokine produced by monocytes and macrophages, and plays an important role in inflammatory responses, development of immune systems, programmed cell death and lipid metabolism. TNF-α is also involved in the development of diseases including asthma, Crohn's disease, rheumatoid arthritis, neuropathic pain, obesity, type II diabetes, autoimmune diseases and tumors. In the immune responses, TNF-α is a multifunctional regulator and even serves as a strong pyrogenic substance to stimulate neutrophil granulocytes, to change the behaviors of vascular endothelial cells, and to regulate the metabolic activity of some tissues.

IFN-γ (interferon γ) is a glycoprotein produced by T cells and natural killer cells in the immune system, and it can activate macrophages to secrete a higher level of proinflammatory cytokines and a lower level of anti-inflammatory cytokines so as to improve bactericidal and tumoricidal activity of macrophages.

A common physical sign among gout patients is that the uric acid concentration in blood increases pathologically. Although not all people with an elevated uric acid level would suffer from gout, each gout patient does have an increased uric acid level. The uric acid concentration increases for two reasons. The first is the reduced urinary excretion of uric acid, and the second one is the enhanced biosynthesis of uric acid due to regulation disorders.

Gout is divided into primary gout and secondary gout. The former is mainly caused by enzyme deficiency, often accompanied by hypertension, diabetes, hyperlipidemia, obesity, metabolic syndrome and coronary heart disease, and may be passed on to his/her offspring. The latter is caused by nephropathy, blood disease, medication and other causes.

If gout is not actively prevented or treated properly, gout will deteriorate with more joints attacked and occur morefrequently, leading to gout based heterogeneous diseases. Urate crystals are deposited on the joints to trigger acute goutarthritis. As multiple joints are attacked at the same time, gout will develop into chronic (long-term) arthritis. Repeated occurrences will cause permanent damages to the joints, including long-term pain and stiffness, limited mobility and joint deformity. When the condition progresses, the crystals will be deposited in soft tissues and then form subcutaneously lumps called "tophi". The deposition of crystals in kidney may cause kidney lesions, leading to acute uric acid nephropathy, chronic urate nephropathy, which causes severe kidney damage and generation of uric acid stones in urinary system.

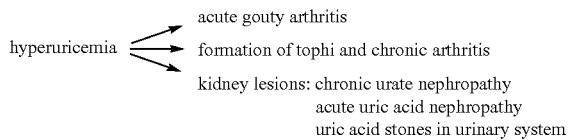

The gouty arthritis is high in incidence, difficult to cure, and occurs over and over. Patients suffer a lot from various complications. This disease is considered as one of the top ten stubborn diseases of the 21$^{st}$ century by World Health Organization.

Many epidemiological studies have so far confirmed that high blood uric acid is an independent risk factor for hypertension. A blood uric acid level increase by 1 mg/dL correlates with an increase of the relative risk of hypertension by 25%. Long-term hyperuricemia may damage pancreatic β-cell's functions and induce diabetes, and studies have shown that there is a causal relationship between long-term hyperuricemia and impaired glucose tolerance as well as diabetes occurrence.

Uric acid level is an independent risk factor for death caused by coronary heart disease. Studies have shown that regardless of gender, uric acid is an independent risk factor for death caused by coronary heart disease. A blood uric acid increase by 1 mg/dL correlates with an increase in the risk of death by 48% for men and 126% for women. Blood uric acid content of more than 6 mg/dL is an independent risk factor for occurrence of coronary heart disease. Blood uric acid content of more than 7 mg/dL is an independent risk factor for stroke occurrence.

Uric acid level and kidney disease are closely related. In addition to the aggravated renal damages resulting from the inflammation at renal arteriolar and chronic inflammation at interstitial caused by the deposition of uric acid crystals, many epidemiological investigations and animal studies have shown that uric acid can directly cause microvascular lesions at afferent arteriolar, leading to chronic kidney disease.

At present, there are limited types of anti-gout agents. Clinical treatment of gout mainly involves the administration of colchicine, agents inhibiting uric acid synthesis (allopurinol, febuxostat), agents promoting uric acid excretion (e.g., probenecid, sulfinpyrazone, benzbromarone, Lesinurad), non-steroidal anti-inflammatory agents and hormones. For acute onset, colchicine, non-steroidal anti-inflammatory agents and hormones are mainly used. When conditions are alleviated, agents inhibiting uric acid synthesis and agents promoting uric acid excretion are mainly used. However, these agents are not so good for treatment because of poor efficacy and adverse side effects.

In 2012, the first-choice uric acid-lowering agents recommended by American College of Rheumatology (ACR) in the Guide to Gout Therapy were allopurinol and febuxostat, wherein febuxostat was recommended for the first time as a first-choice agent. Probenecid serves as a first-choice agent to promote uric acid excretion in the uric acid-lowering treatment only when the patient cannot take or cannot tolerate at least one of the xanthine oxidase inhibitors. In addition, the ACR guidelines recommend the patient starts to receive uric acid-lowering therapy immediately after effective anti-inflammatory therapy begins.

Therefore, there are still needs for new agents for the treatment or prevention of uratic or gouty diseases.

WO2005077950 discloses the compound of general formula (I) of the present invention for treatment of diseases such as dyslipidemia, type II diabetes and the like by activating HM74A (also known as GPR109A). However, this patent does not disclose or suggest that the compound can be useful in the prevention or treatment of uratic or gouty diseases.

WO2011057110 discloses that xanthine derivatives prevent or treat diseases such as cerebral ischemia and the like by activating HM74A.

US20130150383 discloses the use of xanthine compounds for treatment of psoriasis.

US2015080418A1 discloses the use of xanthine compounds in treatment of disorders of nervous tissue.

WO9316699A1 discloses the use of xanthine compounds for treatment of fungal infections.

WO9920280A1 discloses the use of xanthine compounds for treatment of cutaneous itching.

EP0389282A2 discloses the effects of xanthine compounds on brain metabolism, neuroprotection, and vascular abnormalities.

One literature (Expert Opin. Ther Patents 2009, 19 (7), 957-967) discloses that xanthine derivatives activate GPR109A for treatment of dyslipidemia, type II diabetes and some other diseases.

One literature (Curr Atheroscler Rep 2013, 15:325, 1-10) discloses that GPR109A has a pharmacological effect of mediating vascular inflammation.

One literature (PLoS One. 2014 Oct. 17; 9 (10): e109818) indicates that GPR109A is effective in treating Parkinson's disease.

However, none of these literatures has reported the role of xanthine compounds in reducing uric acid level, preventing or treating gout.

SUMMARY OF INVENTION

It is an object of the present invention to provide a novel method for decreasing uric acid level, for preventing or reducing inflammations, and for treating or preventing hyperuricemia, gout, gouty inflammations, pain and uric acid nephropathy.

In order to achieve the above object, the present inventors conducted intensive studies. As a result, it was unexpectedly found that a class of xanthine compounds can reduce uric acid level, and prevent or reduce inflammations so as to effectively prevent or treat hyperuricemia, gout, gouty inflammations, pain and uric acid nephropathy.

Specifically, the present invention relates to the following technical solutions.

(1) Use of a compound of formula (I), a pharmaceutically acceptable salt thereof, a solvate thereof, or a pharmaceutical composition containing the same for reducing uric acid level and for preventing or reducing inflammations and in the manufacture of a medicament for treatment and/or prevention of hyperuricemia, gout, gouty inflammations, pain and uric acid nephropathy,

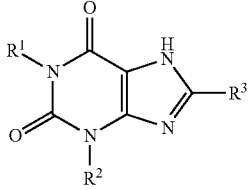

(I)

wherein $R^1$ is selected from a group consisting of hydrogen and $C_{1-4}$ alkyl, wherein said $C_{1-4}$ alkyl is unsubstituted or optionally substituted with one or more halogen, cyano, $CF_3$ or a combination thereof;

$R^2$ is selected from a group consisting of $C_{1-10}$ alkyl, $C_{2-6}$ alkenyl and $C_{2-6}$ alkynyl, wherein said $C_{1-10}$ alkyl, $C_{2-6}$ alkenyl or $C_{2-6}$ alkynyl is unsubstituted or optionally substituted with halogen, cyano, $C_{3-7}$ cycloalkyl or a combination thereof;

$R^3$ is selected from a group consisting of halogen and cyano.

(2) The use according to (1) above, wherein
$R^1$ represents hydrogen or methyl,
$R^2$ represents ethyl, cyclopropylethyl, cyclopropylmethyl, propyl,
2-methylpropyl, butyl, 3-methylbutyl or pentyl,
$R^3$ represents fluorine or chlorine.

(3) The use according to (1) above, wherein the compound is selected from a group consisting of:
8-chloro-3-pentyl-3,7-dihydro-1H-purine-2,6-dione,
8-chloro-3-butyl-3,7-dihydro-1H-purine-2,6-dione,
8-chloro-1-methyl-3-butyl-3,7-dihydro-1H-purine-2,6-dione,
8-chloro-1-methyl-3-pentyl-3,7-dihydro-1H-purine-2,6-dione,
8-chloro-3-(3-methylbutyl)-3,7-dihydro-1H-purine-2,6-dione,
8-chloro-3-(2-cyclopropylethyl)-3,7-dihydro-1H-purine-2,6-dione,
8-chloro-3-(2-methylpropyl)-3,7-dihydro-1H-purine-2,6-dione,
8-chloro-3-(cyclopropylmethyl)-3,7-dihydro-1H-purine-2,6-dione,
8-chloro-1-methyl-3-(3-methylbutyl)-3,7-dihydro-1H-purine-2,6-dione, and
8-chloro-1-methyl-3-(2-cyclopropylethyl)-3,7-dihydro-1H-purine-2,6-dione.

(4) Use of 8-chloro-3-pentyl-3,7-dihydro-1H-purine-2,6-dione, 8-chloro-3-butyl-3,7-dihydro-1H-purine-2,6-dione, 8-chloro-1-methyl-3-butyl-3,7-dihydro-1H-purine-2,6-dione, 8-chloro-1-methyl-3-pentyl-3,7-dihydro-1H-purine-2,6-dione, 8-chloro-3-(3-methylbutyl)-3,7-dihydro-1H-purine-2,6-dione, 8-chloro-3-(2-cyclopropylethyl)-3,7-dihydro-1H-purine-2,6-dione, 8-chloro-3-(2-methylpropyl)-3,7-dihydro-1H-purine-2,6-dione, 8-chloro-3-(cyclopropylmethyl)-3,7-dihydro-1H-purine-2,6-dione, 8-chloro-1-methyl-3-(3-methylbutyl)-3,7-dihydro-1H-purine-2,6-dione, 8-chloro-1-methyl-3-(2-cyclopropylethyl)-3,7-dihydro-1H-purine-2,6-dione, a pharmaceutically acceptable salt thereof, a solvate thereof or a pharmaceutical composition containing the same for reducing uric acid level.

(5) Use of 8-chloro-3-pentyl-3,7-dihydro-1H-purine-2,6-dione, 8-chloro-3-butyl-3,7-dihydro-1H-purine-2,6-dione, 8-chloro-1-methyl-3-butyl-3,7-dihydro-1H-purine-2,6-dione, 8-chloro-1-methyl-3-pentyl-3,7-dihydro-1H-purine-2,6-dione, 8-chloro-3-(3-methylbutyl)-3,7-dihydro-1H-purine-2,6-dione, 8-chloro-3-(2-cyclopropylethyl)-3,7-dihydro-1H-purine-2,6-dione, 8-chloro-3-(2-methylpropyl)-3,7-dihydro-1H-purine-2,6-dione, 8-chloro-3-(cyclopropylmethyl)-3,7-dihydro-1H-purine-2,6-dione, 8-chloro-1-methyl-3-(3-methylbutyl)-3,7-dihydro-1H-purine-2,6-dione, 8-chloro-1-methyl-3-(2-cyclopropylethyl)-3,7-dihydro-1H-purine-2,6-dione, a pharmaceutically acceptable salt thereof, a solvate thereof or a pharmaceutical composition containing the same in preventing or reducing inflammations.

(6) Use of 8-chloro-3-pentyl-3,7-dihydro-1H-purine-2,6-dione, 8-chloro-3-butyl-3,7-dihydro-1H-purine-2,6-dione, 8-chloro-1-methyl-3-butyl-3,7-dihydro-1H-purine-2,6-dione, 8-chloro-1-methyl-3-pentyl-3,7-dihydro-1H-purine-2,6-dione, 8-chloro-3-(3-methylbutyl)-3,7-dihydro-1H-purine-2,6-dione, 8-chloro-3-(2-cyclopropylethyl)-3,7-dihydro-1H-purine-2,6-dione, 8-chloro-3-(2-methylpropyl)-3,7-dihydro-1H-purine-2,6-dione, 8-chloro-3-(cyclopropylmethyl)-3,7-dihydro-1H-purine-2,6-dione, 8-chloro-1-methyl-3-(3-methylbutyl)-3,7-dihydro-1H-purine-2,6-dione, 8-chloro-1-methyl-3-(2-cyclopropylethyl)-3,7-dihydro-1H-purine-2,6-dione, a pharmaceutically acceptable salt thereof, a solvate thereof or a pharmaceutical composition containing the same in the manufacture of a medicament for treatment and/or prevention of hyperuricemia.

(7) Use of 8-chloro-3-pentyl-3,7-dihydro-1H-purine-2,6-dione, 8-chloro-3-butyl-3,7-dihydro-1H-purine-2,6-dione, 8-chloro-1-methyl-3-butyl-3,7-dihydro-1H-purine-2,6-dione, 8-chloro-1-methyl-3-pentyl-3,7-dihydro-1H-purine-2,6-dione, 8-chloro-3-(3-methylbutyl)-3,7-dihydro-1H-purine-2,6-dione, 8-chloro-3-(2-cyclopropylethyl)-3,7-dihydro-1H-purine-2,6-dione, 8-chloro-3-(2-methylpropyl)-3,7-dihydro-1H-purine-2,6-dione, 8-chloro-3-(cyclopropylmethyl)-3,7-dihydro-1H-purine-2,6-dione, 8-chloro-1-methyl-3-(3-methylbutyl)-3,7-dihydro-1H-purine-2,6-dione, 8-chloro-1-methyl-3-(2-cyclopropylethyl)-3,7-dihydro-1H-purine-2,6-dione, a pharmaceutically acceptable salt thereof, a solvate thereof or a pharmaceutical composition containing the same in the manufacture of a medicament for treatment and/or prevention of gout.

(8) Use of 8-chloro-3-pentyl-3,7-dihydro-1H-purine-2,6-dione, 8-chloro-3-butyl-3,7-dihydro-1H-purine-2,6-dione, 8-chloro-1-methyl-3-butyl-3,7-dihydro-1H-purine-2,6-dione, 8-chloro-1-methyl-3-pentyl-3,7-dihydro-1H-purine-2,6-dione, 8-chloro-3-(3-methylbutyl)-3,7-dihydro-1H-purine-2,6-dione, 8-chloro-3-(2-cyclopropylethyl)-3,7- dihydro-1H-purine-2,6-dione, 8-chloro-3-(2-methylpropyl)-3,7-dihydro-1H-purine-2,6-dione, 8-chloro-3-(cyclopropylmethyl)-3,7-dihydro-1H-purine-2,6-dione, 8-chloro-1-methyl-3-(3-methylbutyl)-3,7-dihydro-1H-purine-2,6-dione, 8-chloro-1-methyl-3-(2-cyclopropylethyl)-3,7-dihydro-1H-purine-2,6-dione, a pharmaceutically acceptable salt thereof, a solvate thereof or a pharmaceutical composition containing the same in the manufacture of a medicament for treatment and/or prevention of gouty inflammations.

(9) Use of 8-chloro-3-pentyl-3,7-dihydro-1H-purine-2,6-dione, 8-chloro-3-butyl-3,7-dihydro-1H-purine-2,6-dione, 8-chloro-1-methyl-3-butyl-3,7-dihydro-1H-purine-2,6-dione, 8-chloro-1-methyl-3-pentyl-3,7-dihydro-1H-purine-2,6-dione, 8-chloro-3-(3-methylbutyl)-3,7-dihydro-1H-purine-2,6-dione, 8-chloro-3-(2-cyclopropylethyl)-3,7-dihydro-1H-purine-2,6-dione, 8-chloro-3-(2-methylpropyl)-3,7-dihydro-1H-purine-2,6-dione, 8-chloro-3-(cyclopropylmethyl)-3,7-dihydro-1H-purine-2,6-dione, 8-chloro-1-methyl-3-(3-methylbutyl)-3,7-dihydro-1H-purine-2,6-dione, 8-chloro-1-methyl-3-(2-cyclopropylethyl)-3,7-dihydro-1H-purine-2,6-dione, a pharmaceutically acceptable salt thereof, a solvate thereof or a pharmaceutical composition containing the same in the manufacture of a medicament for treatment and/or prevention of pain.

(10) Use of 8-chloro-3-pentyl-3,7-dihydro-1H-purine-2,6-dione, 8-chloro-3-butyl-3,7-dihydro-1H-purine-2,6-dione, 8-chloro-1-methyl-3-butyl-3,7-dihydro-1H-purine-2,6-dione, 8-chloro-1-methyl-3-pentyl-3,7-dihydro-1H-purine-2,6-dione, 8-chloro-3-(3-methylbutyl)-3,7-dihydro-1H-purine-2,6-dione, 8-chloro-3-(2-cyclopropylethyl)-3,7-dihydro-1H-purine-2,6-dione, 8-chloro-3-(2-methylpropyl)-3,7-dihydro-1H-purine-2,6-dione, 8-chloro-3-(cyclopropylmethyl)-3,7-dihydro-1H-purine-2,6-dione, 8-chloro-1-methyl-3-(3-methylbutyl)-3,7-dihydro-1H-purine-2,6-dione, 8-chloro-1-methyl-3-(2-cyclopropylethyl)-3,7-dihydro-1H-purine-2,6-dione, a pharmaceutically acceptable salt thereof, a solvate thereof or a pharmaceutical composition containing the same in the manufacture of a medicament for the treatment and/or prevention of uric acid nephropathy.

(11) The use according to (1) to (10) above, wherein the hyperuricemia includes primary hyperuricemia and secondary hyperuricemia.

(12) The use according to (1) to (10) above, wherein the gout includes primary gout and secondary gout.

(13) The use according to (1) to (10) above, wherein the gouty inflammation includes acute gouty arthritis, subcutaneous tophi, and chronic tophi arthritis.

(14) The use according to (1) to (10) above, wherein the pain includes acute pain, chronic pain, intractable pain and cancer pain.

(15) The use according to (1) to (10) above, wherein the uric acid nephropathy includes acute uric acid nephropathy, chronic urate nephropathy and uric acid urolithiasis.

(16) A pharmaceutical composition comprising one or more selected from a group consisting of a compound of formula (I), a pharmaceutically acceptable salt thereof and a solvate thereof, and one or more pharmaceutically acceptable carriers.

(17) A compound of formula (I), or a pharmaceutically acceptable salt thereof or a solvate thereof for prevention or treatment of uratic or gouty diseases,

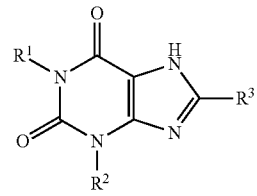

wherein $R^1$ is selected from a group consisting of hydrogen and $C_{1-4}$ alkyl, wherein said $C_{1-4}$ alkyl is unsubstituted or optionally substituted with one or more halogen, cyano, $CF_3$ or a combination thereof;

$R^2$ is selected from a group consisting of $C_{1-10}$ alkyl, $C_{2-6}$ alkenyl and $C_{2-6}$ alkynyl, wherein said $C_{1-10}$ alkyl, $C_{2-6}$ alkenyl or $C_{2-6}$ alkynyl is unsubstituted or optionally substituted with halogen, cyano, $C_{3-7}$ cycloalkyl or a combination thereof;

$R^3$ is selected from a group consisting of halogen and cyano.

(18) The compound according to (17) above, or a pharmaceutically acceptable salt thereof or a solvate thereof, wherein
$R^1$ represents hydrogen or methyl,
$R^2$ represents ethyl, cyclopropylethyl, cyclopropylmethyl, propyl, 2-methylpropyl, butyl, 3-methylbutyl or pentyl,
$R^3$ represents fluorine or chlorine.

(19) The compound according to (17) above, or a pharmaceutically acceptable salt thereof or a solvate thereof, wherein the compound is selected from a group consisting of:
8-chloro-3-pentyl-3,7-dihydro-1H-purine-2,6-dione,
8-chloro-3-butyl-3,7-dihydro-1H-purine-2,6-dione,
8-chloro-1-methyl-3-butyl-3,7-dihydro-1H-purine-2,6-dione, 8-chloro-1-methyl-3-pentyl-3,7-dihydro-1H-purine-2,6-dione, 8-chloro-3-(3-methylbutyl)-3,7-dihydro-1H-purine-2,6-dione, 8-chloro-3-(2-cyclopropylethyl)-3,7-dihydro-1H-purine-2,6-dione, 8-chloro-3-(2-methylpropyl)-3,7-dihydro-1H-purine-2,6-dione, 8-chloro-3-(cyclopropylmethyl)-3,7-dihydro-1H-purine-2,6-dione, 8-chloro-1-methyl-3-(3-methylbutyl)-3,7-dihydro-1H-purine-2,6-dione and 8-chloro-1-methyl-3-(2-cyclopropylethyl)-3,7-dihydro-1H-purine-2,6-dione.

(20) The compound according to any one of (17) to (19) above, or a pharmaceutically acceptable salt thereof or a solvate thereof, which is a hydrate.

(21) The compound according to any one of (17) to (19) above, or a pharmaceutically acceptable salt thereof or a solvate thereof, wherein the uratic or gouty disease is hyperuricemia, gout, gouty inflammation, pain or uric acid nephropathy.

(22) The compound according to any one of (17) to (19) above, or a pharmaceutically acceptable salt thereof or a solvate thereof, for reducing the risk of occurrence of gout, hypertension, diabetes, hyperlipidemia, obesity, metabolic syndrome, coronary heart disease and kidney injury.

(23) The compound according to (21) above, or a pharmaceutically acceptable salt thereof or a solvate thereof, wherein the hyperuricemia includes primary hyperuricemia and secondary hyperuricemia.

(24) The compound according to (21) above, or a pharmaceutically acceptable salt thereof or a solvate thereof, wherein the gout includes primary gout and secondary gout.

(25) The compound according to (21) above, or a pharmaceutically acceptable salt thereof or a solvate thereof, wherein the gouty inflammation includes acute gouty arthritis, subcutaneous tophi, and chronic tophi arthritis.

(26) The compound according to (21) above, or a pharmaceutically acceptable salt thereof or a solvate thereof, wherein the pain includes acute pain, chronic pain, intractable pain and cancer pain.

(27) The compound according to (21) above, or a pharmaceutically acceptable salt thereof or a solvate thereof, wherein the uric acid nephropathy includes acute uric acid nephropathy, chronic urate nephropathy and uric acid urolithiasis.

(28) A compound of formula (I), or a pharmaceutically acceptable salt thereof or a solvate thereof for reducing uric acid level,

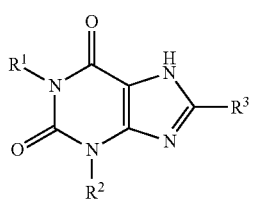
(I)

wherein $R^1$ is selected from a group consisting of hydrogen and $C_{1-4}$ alkyl, wherein said $C_{1-4}$ alkyl is unsubstituted or optionally substituted with one or more halogen, cyano, $CF_3$ or a combination thereof;

$R^2$ is selected from a group consisting of $C_{1-10}$ alkyl, $C_{2-6}$ alkenyl and $C_{2-6}$ alkynyl, wherein said $C_{1-10}$ alkyl, $C_{2-6}$ alkenyl or $C_{2-6}$ alkynyl is unsubstituted or optionally substituted with halogen, cyano, $C_{3-7}$ cycloalkyl or a combination thereof;

$R^3$ is selected from a group consisting of halogen and cyano.

(29) A compound of formula (I), or a pharmaceutically acceptable salt thereof or a solvate thereof for preventing or reducing inflammation,

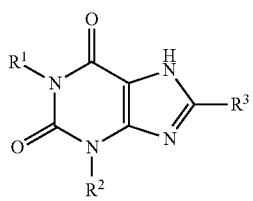
(I)

wherein $R^1$ is selected from a group consisting of hydrogen and $C_{1-4}$ alkyl, wherein said $C_{1-4}$ alkyl is unsubstituted or optionally substituted with one or more halogen, cyano, $CF_3$ or a combination thereof;

$R^2$ is selected from a group consisting of $C_{1-10}$ alkyl, $C_{2-6}$ alkenyl and $C_{2-6}$ alkynyl, wherein said $C_{1-10}$ alkyl, $C_{2-6}$ alkenyl or $C_{2-6}$ alkynyl is unsubstituted or optionally substituted with halogen, cyano, $C_{3-7}$ cycloalkyl or a combination thereof;

$R^3$ is selected from a group consisting of halogen and cyano.

(30) A pharmaceutical composition for prevention or treatment of uratic or gouty diseases comprising a compound of formula (I), a pharmaceutically acceptable salt thereof or a solvate thereof,

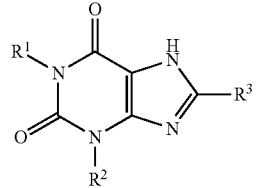
(I)

wherein $R^1$ is selected from a group consisting of hydrogen and $C_{1-4}$ alkyl, wherein said $C_{1-4}$ alkyl is unsubstituted or optionally substituted with one or more halogen, cyano, $CF_3$ or a combination thereof;

$R^2$ is selected from a group consisting of $C_{1-10}$ alkyl, $C_{2-6}$ alkenyl and $C_{2-6}$ alkynyl, wherein said $C_{1-10}$ alkyl, $C_{2-6}$ alkenyl or $C_{2-6}$ alkynyl is unsubstituted or optionally substituted with halogen, cyano, $C_{3-7}$cycloalkyl or a combination thereof;

$R^3$ is selected from a group consisting of halogen and cyano.

(31) The pharmaceutical composition according to (30) above, wherein the uratic or gouty disease is hyperuricemia, gout, gouty inflammation, pain or uric acid nephropathy.

(32) A pharmaceutical composition for reducing uric acid level, which composition comprises a compound of formula (I), a pharmaceutically acceptable salt thereof or a solvate thereof,

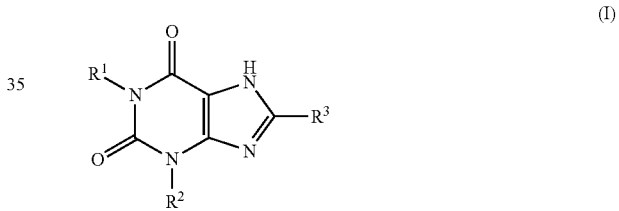
(I)

wherein $R^1$ is selected from a group consisting of hydrogen and $C_{1-4}$ alkyl, wherein said $C_{1-4}$ alkyl is unsubstituted or optionally substituted with one or more halogen, cyano, $CF_3$ or a combination thereof;

$R^2$ is selected from a group consisting of $C_{1-10}$ alkyl, $C_{2-6}$ alkenyl and $C_{2-6}$ alkynyl, wherein said $C_{1-10}$ alkyl, $C_{2-6}$ alkenyl or $C_{2-6}$ alkynyl is unsubstituted or optionally substituted with halogen, cyano, $C_{3-7}$ cycloalkyl or a combination thereof;

$R^3$ is selected from a group consisting of halogen and cyano.

(33) An anti-inflammatory pharmaceutical composition comprising a compound of formula (I), a pharmaceutically acceptable salt thereof or a solvate thereof,

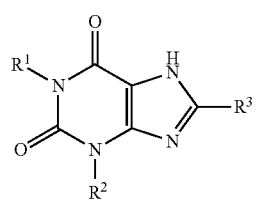
(I)

wherein R¹ is selected from a group consisting of hydrogen and $C_{1-4}$ alkyl, wherein said $C_{1-4}$ alkyl is unsubstituted or optionally substituted with one or more halogen, cyano, $CF_3$ or a combination thereof;

R² is selected from a group consisting of $C_{1-10}$ alkyl, $C_{2-6}$ alkenyl and $C_{2-6}$ alkynyl, wherein said $C_{1-10}$ alkyl, $C_{2-6}$ alkenyl or $C_{2-6}$ alkynyl is unsubstituted or optionally substituted with halogen, cyano, $C_{3-7}$ cycloalkyl or a combination thereof;

R³ is selected from a group consisting of halogen and cyano.

(34) A method for prevention or treatment of uratic or gouty diseases, comprising administering a compound of formula (I), a pharmaceutically acceptable salt thereof or a solvate thereof to a mammal in need thereof,

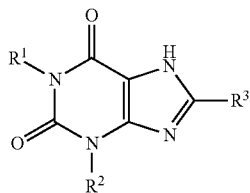

(I)

wherein R¹ is selected from a group consisting of hydrogen and $C_{1-4}$ alkyl, wherein said $C_{1-4}$ alkyl is unsubstituted or optionally substituted with one or more halogen, cyano, $CF_3$ or a combination thereof;

R² is selected from a group consisting of $C_{1-10}$ alkyl, $C_{2-6}$ alkenyl and $C_{2-6}$ alkynyl, wherein said $C_{1-10}$ alkyl, $C_{2-6}$ alkenyl or $C_{2-6}$ alkynyl is unsubstituted or optionally substituted with halogen, cyano, $C_{3-7}$ cycloalkyl or a combination thereof;

R³ is selected from a group consisting of halogen and cyano.

(35) The method according to (34) above, wherein the uratic or gouty disease is hyperuricemia, gout, gouty inflammation, pain or uric acid nephropathy.

(36) A method for reducing uric acid level, comprising administering a compound of formula (I), a pharmaceutically acceptable salt thereof, or a solvate thereof to a mammal in need thereof,

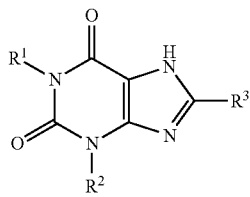

(I)

wherein R¹ is selected from a group consisting of hydrogen and $C_{1-4}$ alkyl, wherein said $C_{1-4}$ alkyl is unsubstituted or optionally substituted with one or more halogen, cyano, $CF_3$ or a combination thereof;

R² is selected from a group consisting of $C_{1-10}$ alkyl, $C_{2-6}$ alkenyl and $C_{2-6}$ alkynyl, wherein said $C_{1-10}$ alkyl, $C_{2-6}$ alkenyl or $C_{2-6}$ alkynyl is unsubstituted or optionally substituted with halogen, cyano, $C_{3-7}$ cycloalkyl or a combination thereof;

R³ is selected from a group consisting of halogen and cyano.

(37) An anti-inflammatory method comprising administering a compound of formula (I), a pharmaceutically acceptable salt thereof or a solvate thereof to a mammal in need thereof,

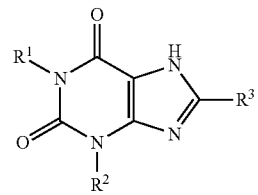

(I)

wherein R¹ is selected from a group consisting of hydrogen and $C_{1-4}$ alkyl, wherein said $C_{1-4}$ alkyl is unsubstituted or optionally substituted with one or more halogen, cyano, $CF_3$ or a combination thereof;

R² is selected from a group consisting of $C_{1-10}$ alkyl, $C_{2-6}$ alkenyl and $C_{2-6}$ alkynyl, wherein said $C_{1-10}$ alkyl, $C_{2-6}$ alkenyl or $C_{2-6}$ alkynyl is unsubstituted or optionally substituted with halogen, cyano, $C_{3-7}$ cycloalkyl or a combination thereof;

R³ is selected from a group consisting of halogen and cyano.

(38) The composition according to any one of (30) to (33) above, further comprising one or more other uric acid-lowering agents, anti-gout agents and anti-inflammatory agents.

(39) A kit comprising: a composition according to any one of (30) to (33) above, and an instruction with one or more types of information, the information being selected from a group consisting of information about the conditions which the pharmaceutical composition is suitable for treating, information for storage of the pharmaceutical composition, administration information, and information on how to administer the pharmaceutical composition.

The technical solutions above of the present invention have an anti-inflammatory effect, and can inhibit the occurrence and development of inflammations in the patients with high levels of uric acid and alleviate the inflammatory responses in the patients with gout, tophi, gouty inflammation and uric acid nephropathy. These technical solutions are also effective in reducing uric acid level, and thus can further reduce the occurrence risk of gout, hypertension, diabetes, hyperlipidemia, obesity, metabolic syndrome, coronary heart disease and kidney injury, thereby alleviating the pain of patients and treating or preventing uratic or gouty diseases.

In particular, the inflammatory response is a condition resulting from the elevation of uric acid level while the compound of the present invention has an unexpected effect of reducing uric acid level. Therefore, the compound of the present invention can fundamentally alleviate the inflammatory responses induced by the increase of uric acid, thereby exhibiting an anti-inflammatory effect.

DETAILED DESCRIPTIONS OF EMBODIMENTS

The terms used in the present specification have the following meanings.

The term "halogen" refers to a fluorine atom, a chlorine atom, a bromine atom, an iodine atom and the like. A fluorine atom and a chlorine atom are preferred.

The term "$C_{1-10}$ alkyl" represents a straight or branched alkyl group having 1 to 10 carbon atoms, preferably a $C_{1-6}$ alkyl group having 1 to 6 carbon atoms. Said "$C_{1-10}$ alkyl" may be methyl, ethyl, n-propyl, isopropyl, n-butyl, isobutyl, sec-butyl, tert-butyl, n-pentyl, isopentyl, 2-methylbutyl, neopentyl, 1-ethylpropyl, n-hexyl, isohexyl, 3-methylpentyl, 2-methylpentyl, 1-methylpentyl, 3,3-dimethylbutyl, 2,2-dimethylbutyl, 1,1-dimethylbutyl, 1,2-dimethylbutyl, 1,3-dimethylbutyl, 2,3-dimethylbutyl, 2-ethylbutyl, 1,2-dimethylpropyl, heptyl, octyl, nonyl, decyl and the like.

The term "$C_{1-4}$ alkyl" represents a straight or branched alkyl group having 1 to 4 carbon atoms, such as methyl, ethyl, n-propyl, isopropyl, n-butyl, isobutyl, sec-butyl, t-butyl and the like.

The term "$C_{2-6}$ alkenyl" refers to a straight or branched alkenyl group having 2 to 6 carbon atoms and containing a double bond, such as vinyl, 1-propenyl, 2-propenyl, 1-methylvinyl, 1-butenyl, 2-butenyl, 3-butenyl, 1-methyl-1-propenyl, 2-methyl-1-propenyl, 1-methyl-2-propenyl, 2-methyl-2-propenyl, 1-pentenyl, 2-pentenyl, 3-pentenyl, 4-pentenyl, 1-methyl-1-butenyl, 2-methyl-1-butenyl, 3-methyl-1-butenyl, 1-methyl-2-butenyl, 2-methyl-2-butenyl, 3-methyl-2-butenyl, 1-methyl-3-butenyl, 2-methyl-3-butenyl, 3-methyl-3-butenyl, 1,1-dimethyl-2-propenyl, 1,2-dimethyl-1-propenyl, 1,2-dimethyl-2-propenyl, 1-ethyl-1-propenyl, 1-ethyl-2-propenyl, 1-hexenyl, 2-hexenyl, 3-hexenyl, 4-hexenyl, 5-hexenyl, 1-methyl-1-pentenyl, 2-methyl-1-pentenyl, 3-methyl-1-pentenyl, 4-methyl-1-pentenyl, 1-methyl-2-pentenyl, 2-methyl-2-pentenyl, 3-methyl-2-pentenyl, 4-methyl-2-pentenyl, 1-methyl-3-pentenyl, 2-methyl-3-pentenyl, 3-methyl-3-pentenyl, 4-methyl-3-pentenyl, 1-methyl-4-pentenyl, 2-methyl-4-pentenyl, 3-methyl-4-pentenyl, 4-methyl-4-pentenyl, 1,1-dimethyl-2-butenyl, 1,1-dimethyl-3-butenyl, 1,2-dimethyl-1-butenyl, 1,2-dimethyl-2-butenyl, 1,2-dimethyl-3-butenyl, 1,3-dimethyl-1-butenyl, 1,3-dimethyl-2-butenyl, 1,3-dimethyl-2-butenyl, 2,2-dimethyl-3-butenyl, 2,3-dimethyl-1-butenyl, 2,3-dimethyl-2-butenyl, 2,3-dimethyl-3-butenyl, 3,3-dimethyl-1-butenyl, 3,3-dimethyl-2-butenyl, 1-ethyl-1-butenyl, 1-ethyl-2-butenyl, 1-ethyl-3-butenyl, 2-ethyl-1-butenyl, 2-ethyl-2-butenyl, 2-ethyl-3-butenyl, 1,1,2-trimethyl-2-propenyl, 1-ethyl-1-methyl-2-propenyl, 1-ethyl-2-methyl-1-propenyl, 1-ethyl-2-methyl-2-propenyl, 1,3-butadienyl, 1,3-pentadienyl, 1,4-pentadienyl, 2,4-pentadienyl, 1,4-hexadienyl, 2,4-hexadienyl, and the like. The $C_{1-4}$ alkyl with the double bond may optionally be cis- or trans-isomer.

The term "$C_{2-6}$ alkynyl" refers to a straight or branched alkynyl group having 2 to 6 carbon atoms and containing a triple bond, such as ethynyl, 1-propynyl, 2-propynyl, 2-butynyl, 3-butynyl, 1-methyl-2-propynyl, 2-pentynyl, 3-pentynyl, 4-pentynyl, 1-methyl-2-butynyl, 1-methyl-3-butynyl, 2-methyl-3-butynyl, 1,1-dimethyl-2-propynyl, 1-ethyl-2-propynyl, 2-hexynyl, 3-hexynyl, 4-hexynyl, 5-hexynyl, 1-methyl-2-pentynyl, 4-methyl-2-pentynyl, 1-methyl-3-pentynyl, 2-methyl-3-pentynyl, 1-methyl-4-pentynyl, 2-methyl-4-pentynyl, 3-methyl-4-pentynyl, 1,1-dimethyl-2-butynyl, 1,1-dimethyl-3-butynyl, 1,2-dimethyl-3-butynyl, 2,2-dimethyl-3-butynyl, 1-ethyl-2-butynyl, 1-ethyl-3-butynyl, 2-ethyl-3-butynyl and 1-ethyl-1-methyl-2-propynyl and the like.

The term "3-7 membered cycloalkyl" refers to a cyclic alkyl group derived from an alkane moiety having 3 to 7 carbon atoms with one hydrogen atom removed wherefrom, including monocyclic cycloalkyl, fused cycloalkyl, bridged cyclic group and spiro-cyclic group.

The term "monocyclic cycloalkyl" refers to a 3- to 7-membered monocyclic cycloalkyl, including 3- to 7-membered saturated monocyclic cycloalkyl and 3- to 7-membered partially saturated monocyclic cycloalkyl. The "3- to 7-membered saturated monocyclic cycloalkyl" means that the monocyclic ring is a fully saturated carbocyclic ring, and examples thereof include, but are not limited to, cyclopropyl, cyclobutyl, cyclopentyl, cyclohexyl, cycloheptyl, cyclooctyl, methylcyclopropyl, dimethylcyclopropyl, methylcyclobutyl, dimethylcyclobutyl, methylcyclopentyl, dimethylcyclopentyl, methylcyclohexyl, dimethylcyclohexyl and the like. The "3- to 7-membered partially saturated monocyclic cycloalkyl" means that the monocyclic ring is a partially saturated carbocyclic ring, and examples thereof include, but are not limited to, cyclopropenyl, cyclobutenyl, cyclopentenyl, cyclohexenyl, 1,4-cyclohexadienyl, cycloheptenyl, 1,4-cycloheptadienyl, cyclooctenyl, 1,5-cyclooctadienyl and the like.

The term "fused cycloalkyl" refers to a fused cycloalkyl group formed by two or more cyclic structures with adjacent two cyclic structures sharing two adjacent carbon atoms with each other, including 6-7 membered saturated fused cyclic groups and 6-7 membered partially saturated fused cyclic groups. Examples of 6-7 membered saturated fused cyclic groups include, but are not limited to, bicyclo[3.1.0]hexyl, bicyclo[4.1.0]heptyl, bicyclo[2.2.0]hexyl, bicyclo[3.2.0]heptyl, bicyclo[4.2.0]octyl and the like. The 6-7 membered partially saturated fused cycloalkyl groups refer to the groups in which at least one ring in the fusedcyclic ring is a partially saturated carbocyclic ring, examples of which include, but are not limited to, bicyclo[3.1.0]hex-2-enyl, bicyclo[4.1.0]hept-3-enyl, bicyclo[3.2.0]hept-3-enyl, bicyclo[4.2.0]oct-3-enyl and the like.

The term "mammal" is preferably a human.

The term "treatment" refers to the complete or partial alleviation of symptoms associated with a disorder or disease, or slowing down or suspending the further development or progression of these symptoms.

The term "prevention" means prevention of the disease or disorder from occurring in a subject at risk of developing the disease or disorder.

The term "uratic disease" refers to a disease associated with an abnormal uric acid level in an organism, including but not limited to hyperuricemia or uric acid nephropathy.

The term "gouty disease" refers to a disease associated with gout, including but not limited to gout, gouty inflammations, or pain.

Primary hyperuricemia is divided into hyperuricemia with molecular defects and congenital purine metabolism disorder, both with unknown causes. The congenital purine metabolism disorder is divided into the following four types:

(I) In the first type, the activity of 5-phosphoribosyl-1-pyrophosphate synthase (PRPPS) increases, causing excessive synthesis of 5-phosphoribosyl-1 pyrophosphate synthase and excessive generation of uric acid. This type of disorder is X-linked in inheritance.

(II) In the second type, hypoxanthine-guanine phosphoribosyltransferase (HPRT) is partially deficient, causing increased concentration of 5-phosphoribosyl-1-pyrophosphate synthase and excessive generation of uric acid. This type of disorder is also X-linked in inheritance.

(III) In the third type, hypoxanthine-guanine phosphoribosyltransferase is completely deficient, and too much uric acid is produced due to the increased purine synthesis, which is found in Lesch-Nyhan syndrome. The type of disorder is X-linked in inheritance.

(IV) In the fourth type, glucose-6-phosphatase is deficient so that excessive uric acid is produced due to increased purine synthesis and reduced clearance of uric acid by kidney, which is usually found in Glycogen storage disease type I. The type of disorder belongs to autosomal recessive inheritance.

Secondary hyperuricemia refers to hyperuricemia caused by 1) increased blood uric acid level resulting from a variety of acute or chronic diseases such as blood disease or malignancies, chronic poisoning, administration of medication or high-purine diet, or by 2) uric acid excretion disorder.

Gout is a crystal-related arthropathy caused by deposition of sodium urate (MSU) and is directly associated with hyperuricemia due to purine metabolism disorders and/or decreased uric acid excretion. Gout especially refers to acute arthritis and chronic tophi disease, mainly including acutely occurred arthritis, tophi formation, chronic tophi arthritis, urate nephropathy and uric acid urolithiasis. In severe cases, joint deformity and renal insufficiency may occur.

Primary gout is mostly hereditary, but clinically only 10% to 20% of patients have a family history of gout. Generation of too much uric acid accounts for 10% of the causes of primary hyperuricemia. The main causes are enzyme deficiency in purine metabolic, lack of hypoxanthine guanine phosphoribosyl transferase (HGPRT) and excessive activity of phosphate ribose pyrophosphate (PRPP) synthase. Primary reduction of uric acid excretion in kidney leads to about 90% of primary hyperuricemia. Although the underlying mechanism is unclear and it may be a polygenic hereditary disease, it cannot be a kind of organic diseases of the kidney.

Secondary gout refers to a clinical manifestation secondary to other diseases or caused by certain agents. Myeloproliferative diseases such as leukemia, lymphoma, multiple myeloma, erythrocytosis, hemolytic anemia and cancers may lead to accelerated cell proliferation, thereby causing increased nucleic acid conversion to induce increased production of uric acid. Radiotherapy and chemotherapy against malignant tumors causes damage to a large number of cells and increase of nucleic acid conversion, thus increasing production of uric acid. Kidney diseases, including chronic glomerulonephritis, pyelonephritis, polycystic kidney disease, and glomerular hypo-filtration caused by lead poisoning, hypertension at late stage and the like, may reduce uric acid excretion, leading to the increased blood uric acid concentration. Agents, such as thiazide diuretics, furosemide, ethambutol, pyrazinamide, aspirin at a low dose and nicotinic acid and the like, compete with uric acid to inhibit excretion of uric acid by renal tubule and cause hyperuricemia. In addition, the long-term administration of immunosuppressive agents can also lead to hyperuricemia in kidney transplant recipients, which may be related to the immunosuppressive agents' inhibitory effect on uric acid excretion by renal tubule.

Gouty inflammation is the lesion and inflammatory response caused by urate deposition on the joint capsule, bursa, cartilage, bone and other tissues. The onset of gouty inflammation is affected by genetic factors and family factors to a great extent, and mostly occurs in men over the age of 40. Such inflammation usually occurs in the metatarsophalangeal joint of the hallux, and also occurs in other larger joints especially joints at the ankle and foot. The main manifestation is the sharp pain at joints, which often outbreaks unilaterally in a sudden way. The surrounding tissues of joints become markedly swollen, hot, red and tender.

With regard to acute gouty arthritis, there is no obvious sign before onset in most patients, and patients only feel tired, uncomfortable and stabbing pain at joints. Acute gouty arthritis typical occurs in mid-night, and the patients are often awakened due to joint pain. The pain aggravates progressively, reaching a peak in about 12 hours. The patients feel as if being torn, cut by a knife or bitten by someone, which is unbearable. Affected joints and surrounding tissues become red, swollen, hot and painful with limited functions. The symptoms disappear spontaneously after a few days or 2 weeks in most cases. The first onset often occurs in a single joint, mostly in the first metatarsophalangeal joint. In future courses, this position is involved in some patients. The joints affected subsequently are those at dorsal foot, heel, ankle, knee, wrist and elbow. The joints at shoulder, hip and spine and temporomandibular joint are mildly involved. Multiple joints may be involved at the same time, exhibiting as polyarthritis. Some patients may have systemic symptoms like fever, chills, headache, palpitations and nausea, accompanied with the increased level of leukocytes, increased erythrocyte sedimentation rate, increased level of C-reactive protein and so on.

With regard to intermittent onsets, gout attacks would disappear spontaneously after lasting for several days to several weeks, usually without significant sequelae, or with only local skin pigmentation, desquamation, itching and etc. Thereafter, gout enters the intermission without any episode, which lasts for several months, several years or more than ten years before relapse. The majority of patients suffer from recurrence within 1 year, for whom the onset is more and more frequent, with more and more joints involved for longer and longer duration. Involved joints generally develop from lower limbs to upper limbs and from distal small joints to large joints. Gradually, the finger, wrist and elbow joints are involved. In a small number of patients, joints at shoulder, coxa, sacroiliac, sternoclavicular or spine may be affected, as well as parts such as bursa, tendon and tendon sheath adjacent to joints with symptoms tending to be atypical. A small number of patients have no intermission and develop into chronic arthritis after the initial onset.

With regard to chronic tophi, in the onset, nodules as hard as stone, known as "tophi", also known as gout nodules are generated in gout patients. Subcutaneous tophi and chronic tophi arthritis are the result of long-term severe hyperuricemia with deposition of large amounts of sodium urate crystals in the subcutaneous tissues, synovial membrane, cartilage, bone and soft tissues around joints.

Such sodium urate crystals are deposited in soft tissues, causing chronic inflammation and nodules formed due to fibrous tissue hyperplasia. Tophi is found in helix most commonly, also commonly found in the first metatarsophalangeal joint of hallux, joints at finger, wrist, elbow and knee, etc. In a small number of patients, tophi may appear in nasal cartilage, tongue, vocal cord, eyelid, aorta, cardiac valve and myocardium. The tophi may invade into the bone in the skeleton around joints, causing skeletal deformities. Alternatively, tophi may destroy bone. Such gout nodules can also be found in synovial membrane, tendon sheath and cartilage near joints. The sizes of tophi are different, which may be as small as sesame or as large as eggs.

Tophi may also be formed in internal organs, mainly in the renal parenchyma, sometimes in ureter and bladder, but rare in liver, gallbladder, biliary tract and pancreas, etc. Urate crystals have been reported to be found in saliva. No tophus has been ever found in brain, spleen or lung. After appearance, tophi will grow in size from small to large gradually and the amount of urate crystals gradually increases so that the internal pressure rises, which often makes local skin swollen, tense, thin and shiny. In combination with the erosion by urate crystals, the integrity of the covering skin is destroyed and stretchability deteriorates. The skin may ulcerate if rubbed, pressed, frozen or wounded. The "toothpaste-like" white urate crystals will leak out from the skin ulcer. Sinus or rash tube may be formed at the ulcer. Chronic inflammatory granuloma will be formed at the tissues around the ulcer due to the stimulation of urate crystals, where secondary bacterial infection may possibly occur to form chronic suppurative focuses. It is difficult for ulceration to self-heal due to poor blood circulation and weak cell regeneration, as well as infection and chronic granulomatosis and other reasons. Sepsis can be caused in severe cases, leading to death.

Tophi are characteristic marks of gout. The formation of tophi is related with course of disease and blood uric acid level. The longer the course is, the more likely the tophi will be formed. The longer the hyperuricemia lasts, the more likely the tophi will be formed. On the other hand, a great number and a large size of tophi indicates that hyperuricemia has not been well controlled, that is, the condition becomes severer. For some patients, although the course is already very long, the blood uric acid level is maintained in the normal range for a long time after treatment, rarely with the formation of tophi. The presence of tophi and the number and size of tophi are also intuitive indicators for the clinical judgment of the severity of the condition and fitness of treatment.

The typical site where subcutaneous tophi are formed is auricle. Subcutaneous tophi are also commonly found in sites such as parts around joints and olecranon, achilles tendon and patella bursa where conditions occur repeatedly. Subcutaneous tophi are yellowish-white neoplasms of various sizes uplifting under the skin with the skin being thin, where white powder or paste is discharged after the skin ulcerates which is unhealed for a long time.

Subcutaneous tophi and chronic tophi arthritis often coexist. The deposition of a large amount of tophi in joints may cause bone destruction in joints, fibrosis of tissues around joints and secondary degenerative conditions. Clinical manifestations are persistent swelling and pain of joints, pain upon pressing, deformity and dysfunction. Chronic symptoms are relatively moderate, but may occur in an acute manner.

Uric acid nephropathy is the kidney injury caused by hyperuricemia due to excessive production or reduced excretion of blood uric acid, often referred to as gouty nephropathy. Clinical manifestations may include uric acid stones, proteinuria, edema, nocturia, hypertension, increased blood uric acid level and renal tubular damage. This kind of disease is quite common in Western countries, while in China, more patients are found in the north. The disease does not follow an obvious seasonal pattern, and is likely to occur in those having a weight problem or being fond of carnivorous diets and alcohol. The ratio of male to female patients is 9:1 with 85% being the middle-aged and old people. If a patient is diagnosed for the disease at the early stage and is provided with appropriate treatments (to control hyperuricemia and to protect kidney function), kidney injury can be alleviated prevented from developing. If the treatment is not timely or properly provided, the disease may deteriorate and develop into the end-stage renal failure where dialysis is needed.

With regard to chronic urate nephropathy, urate crystals are deposited in renal interstitium, leading to chronic tubulointerstitial nephritis. Clinical manifestations include the decreased urinary concentration function, severe nocturia, production of low specific gravity urine, proteinuria, leukocyturia, mild hematuria and cylindruria. In the late stage, the filtration function of glomeruli may be damaged, resulting in renal insufficiency.

With regard to uratic stones in urinary tract, the concentration of uric acid in urine is increased to an over-saturated state. Uric acid is deposited in the urinary system to form stones, which occurs in more than 20% of the patients of gout and possibly before the occurrence of gouty arthritis. Small stones look like sands and are discharged with urine, with no obvious symptom. The larger stones may block the urinary tract, causing renal colic, hematuria, dysuria, urinary system infection, pyelectasis and hydronephrosis, and etc.

There are many factors affecting the formation of kidney stones, including age, gender, race, genetic factors, environmental factors, diet habits and occupation, which are all related with the formation of stones. The body's abnormal metabolism, urinary obstruction, infection at urinary tract, foreign matters and medication are the common causes of stone formation. Urinary calculi have been known to have 32 kinds of ingredients, wherein the most common ingredient is calcium oxalate. Other ingredients of stones are, for example, magnesium ammonium phosphate, uric acid, calcium phosphate and cystine (an amino acid), etc., and can also be a mixture of the above ingredients. As to urate stones, the urine is continuously acidic. The urate stones are hard, smooth, granular, yellow or brownish red, and the metabolism of uric acid is abnormal.

For acute uric acid nephropathy, uric acid levels in blood and urine increase sharply. A large number of uric acid crystals are deposited in the renal tubules, collecting tubule and so on, resulting in acute urinary obstruction. Clinical manifestations are oliguria, anuria and acute renal failure. Further, a large number of uric acid crystals can be found in urine. These are secondary conditions mostly caused by malignant tumors and the radiotherapy and chemotherapy thereof (i.e., tumor lysis syndrome).

In case of the increase in blood uric acid level, the crystal deposition in joints may cause gouty arthritis, and further cause joint deformities. Crystal deposition in kidney may cause gouty nephropathy and uric acid stones, further causing uremia. The increase in blood uric acid level may stimulate the arterial wall, and cause atherosclerosis and aggravate coronary heart disease and hypertension. The increase in blood uric acid may damage the pancreatic B cells, thereby inducing or aggravating diabetes.

Hyperuricemia is the basis for the onset of gout, but not sufficient to cause gout. Gout takes place only when urates are deposited in body tissues and cause damages. The higher the level of blood uric acid is, the more likely gout will occur in the next 5 years.

In the present invention, $R^1$ is selected from a group consisting of hydrogen and $C_{1-4}$ alkyl, wherein said $C_{1-4}$ alkyl is unsubstituted or optionally substituted with one or more halogen, cyano, $CF_3$ or a combination thereof. More preferably, $R^1$ is selected from a group consisting of hydrogen and unsubstituted $C_{1-4}$ alkyl group. Still more preferably, $R^1$ is selected from a group consisting of hydrogen, methyl and ethyl. Most preferably, $R^1$ is hydrogen or methyl.

$R^2$ is selected from a group consisting of $C_{1-10}$ alkyl, $C_{2-6}$ alkenyl and $C_{2-6}$ alkynyl, wherein said $C_{1-10}$ alkyl, $C_{2-6}$ alkenyl or $C_{2-6}$ alkynyl is unsubstituted or optionally substituted with halogen, cyano, $C_{3-7}$ cycloalkyl or a combination thereof. $R^2$ is more preferably $C_{1-6}$ alkyl, and further preferably ethyl, cyclopropylethyl, cyclopropylmethyl, propyl, 2-methylpropyl, butyl, 3-methylbutyl or pentyl. $R^2$ is more preferably $C_{3-6}$ alkyl, further more preferably $C_{4-5}$ alkyl, and most preferably butyl or pentyl.

$R^3$ is selected from a group consisting of halogen and cyano. $R^3$ is preferably halogen, more preferably fluorine, chlorine or bromine, still more preferably fluorine or chlorine, and most preferably chlorine.

The preferred embodiments described above are by no means an exhaustive list with respect to the definitions of $R^1$, $R^2$ and $R^3$ in formula (I) of the present invention, and the technical solutions with some groups in the definitions and various preferred embodiments omitted are all included in the scope of the present invention. Moreover, the combinations of the above-mentioned definitions of $R^1$, $R^2$ and $R^3$, various preferred embodiments, and the technical solutions with the substituents in the various preferred embodiments omitted are also within the scope of the present invention.

As one preferred embodiment of the present invention, $R^1$ is selected from a group consisting of hydrogen and $C_{1-4}$ alkyl; $R^2$ is selected from a group consisting of $C_{1-10}$ alkyl, $C_{2-6}$ alkenyl, and $C_{2-6}$ alkynyl; $R^3$ is selected from a group consisting of halogen and cyano.

As another preferred embodiment of the present invention, $R^1$ is selected from a group consisting of hydrogen and $C_{1-4}$ alkyl; $R^2$ is $C_{1-10}$ alkyl; $R^3$ is selected from a group consisting of halogen and cyano.

As another preferred embodiment of the present invention, $R^1$ is selected from a group consisting of hydrogen and $C_{1-4}$ alkyl; $R^2$ is $C_{1-6}$ alkyl; $R^1$ is halogen.

As another preferred embodiment of the present invention, $R^1$ represents hydrogen or methyl; $R^2$ represents ethyl, cyclopropylethyl, cyclopropylmethyl, propyl, 2-methylpropyl, butyl, 3-methylbutyl or pentyl; and $R^3$ represents fluorine or chlorine.

As another preferred embodiment of the present invention, $R^1$ represents hydrogen or methyl; $R^2$ represents propyl, 2-methylpropyl, butyl, 3-methylbutyl or pentyl; and $R^3$ represents fluorine or chlorine.

As another preferred embodiment of the present invention, $R^1$ represents hydrogen or methyl, $R^2$ represents propyl, butyl or pentyl, and $R^3$ represents chlorine.

Preferred examples of the compounds of the present invention are:
8-chloro-3-pentyl-3,7-dihydro-1H-purine-2,6-dione,
8-chloro-3-butyl-3,7-dihydro-1H-purine-2,6-dione,
8-chloro-1-methyl-3-butyl-3,7-dihydro-1H-purine-2,6-dione, 8-chloro-1-methyl-3-pentyl-3,7-dihydro-1H-purine-2,6-dione, 8-chloro-3-(3-methylbutyl)-3,7-dihydro-1H-purine-2,6-dione, 8-chloro-3-(2-cyclopropylethyl)-3,7-dihydro-1H-purine-2,6-dione, 8-chloro-3-(2-methylpropyl)-3,7-dihydro-1H-purine-2,6-dione, 8-chloro-3-(cyclopropylmethyl)-3,7-dihydro-1H-purine-2,6-dione, 8-chloro-1-methyl-3-(3-methylbutyl)-3,7-dihydro-1H-purine-2,6-dione and 8-chloro-1-methyl-3-(2-cyclopropylethyl)-3,7-dihydro-1H-purine-2,6-dione.

The pharmaceutically acceptable salt of the compound represented by formula (I) is, for example, a salt formed with the alkali metal, alkaline earth metal, ammonium, alkylammonium or the like, or a salt formed with an inorganic acid or an organic acid. These salts can be, for example, sodium salts, potassium salts, calcium salts, ammonium salts, aluminum salts, triethylammonium salts, acetates, propionates, butyrates, formates, trifluoroacetates, maleates, tartrates, citrates, stearates, succinates, ethylsuccinates, lactobionates, gluconates, gluceptates, benzoates, methanesulfonates, ethanesulfonates, 2-hydroxyethanesulfonates, benzenesulfonates, p-toluenesulfonates, laurylsulfates, malates, aspartates, glutamates, adipates, trihydroxymethylaminomethane salts, salts formed with cysteine, salts formed with N-acetylcysteine, hydrochlorides, hydrobromides, phosphates, sulfates, hydroiodates, nicotinates, oxalates, picrates, thiocyanates, undecanoates, salts formed with acrylic acid polymers, salts formed with carboxyvinyl polymers, and the like.

The solvate of the compound represented by formula (I) or a salt thereof may be, for example, a hydrate or the like, but is not limited thereto. The hydrate is preferably a monohydrate.

In addition, among the compounds represented by formula (I) of the present invention, if any chiral carbon is present, the present invention includes isomers formed with any stereoconfiguration related to the chiral carbon, including, for example, racemates or any mirror-image isomers. Furthermore, the invention encompasses all other possible stereoisomers. That is, the compounds of the present invention include all enantiomers, diastereomers, various forms of compounds in dissociation equilibrium, mixtures of the above in any ratio therebetween or thereamong, racemates and the like.

The compound of formula (I) of the present invention can be produced according to various known methods, i.e., the method is not particularly limited. For example, the compound of formula (I) can be prepared according to the following reaction steps, as described in the following reaction route diagram, but the preparation method is not limited thereto.

Reaction Route Diagram

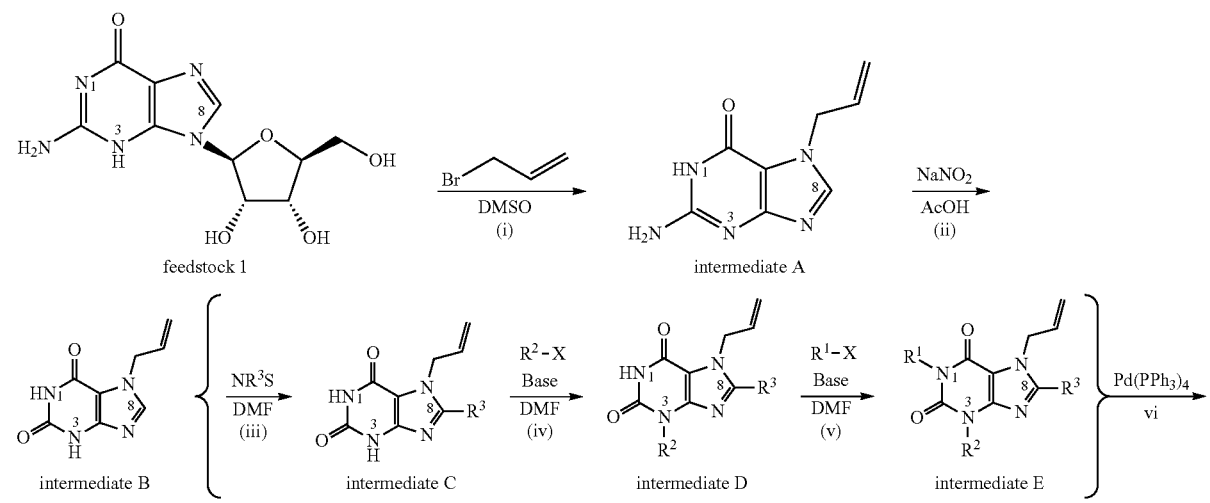

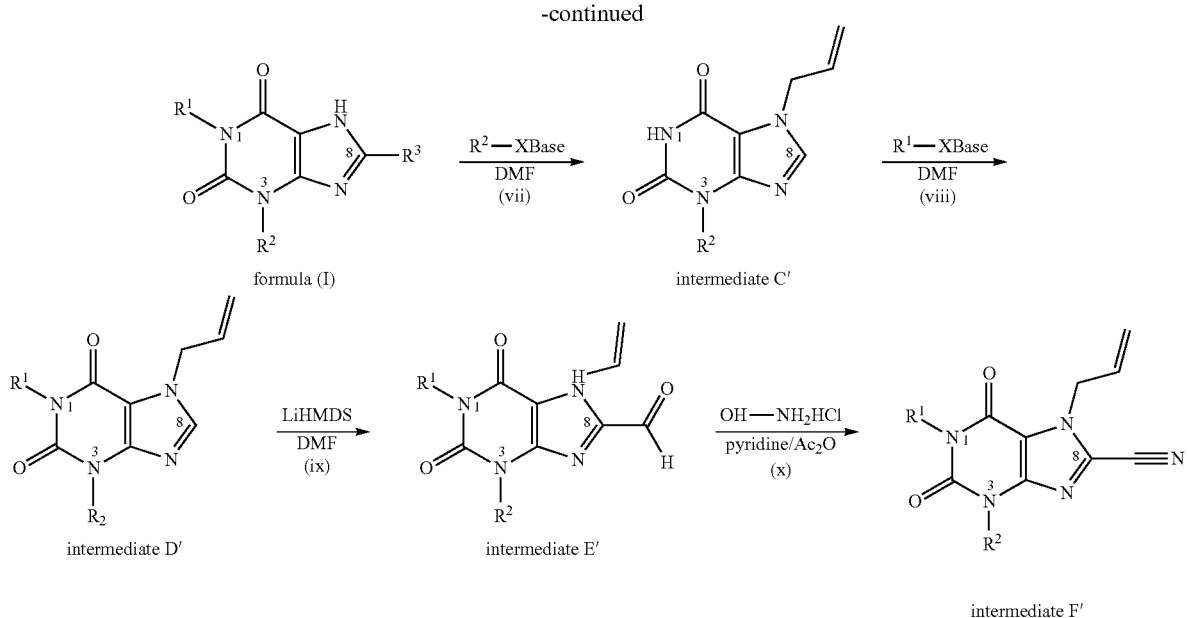

(wherein, $R^1$, $R^2$ and $R^3$ are defined as above, and X represents halogen.)

i) Alkylation of feedstock 1 with allyl bromide;
ii) Diazotization using sodium nitrite followed by hydrolysis to form intermediate B;
iii) Halogenation of $C_8$ with halosuccinimide, wherein $R^3$ represents —F, —Cl, —Br, or —I;
iv) Alkylation at $N^3$, wherein $R^2$ represents hydrogen or alkyl;
v) Alkylation at $N^1$, wherein $R^1$ represents an alkane group;
vi) Removal of allyl;
vii) Alkylation at $N^3$, wherein $R^2$ represents an alkane group;
viii) Alkylation at $N^1$, wherein $R^1$ represents an alkane group;
ix) Formation of aldehyde group at $C^8$;
x) Conversion of the aldehyde to nitrile.

In particular, as shown in the above reaction route, when $R^3$ represents halogen, feedstock 1 is alkylated with allyl bromide at a temperature of 0-50° C., preferably 20-30° C. in a solvent such as DMSO, DMF, acetone, dioxane, acetonitrile, tetrahydrofuran or N-methylpyrrolidone, preferably in DMSO, to give an intermediate A. The diazotization is then carried out using sodium nitrite at a temperature of 0-100° C., preferably 20-60° C., in a system formed by an acid at a low concentration (such as acetic acid, dilute hydrochloric acid or dilute sulfuric acid) and water, followed by hydrolysis to form an intermediate B. Intermediate B is halogenated with halosuccinimide in DMF, DMSO, dioxane, acetonitrile, tetrahydrofuran or N-methylpyrrolidone at a temperature of 0-100° C., preferably 20-60° C., to give an intermediate C. Intermediate C is alkylated using a halohydrocarbon in the presence of a base in DMF, DMSO, dioxane, acetonitrile, tetrahydrofuran or N-methylpyrrolidone at a temperature of 0-50° C., preferably 25° C., to give an intermediate D, wherein the step for preparing intermediate D can precede the step for preparing intermediate C. When $R^1$ represents alkyl, the intermediate D is alkylated using a halohydrocarbon in the presence of a base in DMF, DMSO, dioxane, acetonitrile, tetrahydrofuran or N-methylpyrrolidone at a temperature of 0 to 120° C., preferably 50 to 100° C., to give an intermediate E. The intermediate D ($R^1$ represents hydrogen) or the intermediate E ($R^1$ represents alkyl) is added with morpholine or 1,3-dimethylbarbituric acid under the protection of an inert gas in dichloromethane, chloroform, carbon tetrachloride or acetone at a temperature of 0 to 60° C., preferably 20 to 30° C., and allyl is removed under the catalysis of a palladium catalyst or without a catalyst to obtain a compound represented by formula (I).

When $R^3$ represents a cyano group, the intermediate B is alkylated using a halohydrocarbon in the presence of a base in DMF, DMSO, dioxane, acetonitrile, tetrahydrofuran or N-methylpyrrolidone at 0-50° C., preferably 25° C., to give an intermediate C'. Intermediate C' is alkylated using a halohydrocarbon in the presence of a base in DMF, DMSO, dioxane, acetonitrile, tetrahydrofuran or N-methylpyrrolidone at 0 to 120° C., preferably 50 to 100° C., to give an intermediate D'. Intermediate D' is subjected to elimination reaction by use of LiHMDS or NaHMDS, and is then quenched with DMF, an alcohol or water to give an intermediate E'. Intermediate E' is converted to an intermediate F' in acetic anhydride, toluene or benzene under the action of hydroxylamine hydrochloride and pyridine. Intermediate F' is added with morpholine or 1,3-dimethylbarbituric acid under the protection of an inert gas in dichloromethane, chloroform, carbon tetrachloride or acetone at a temperature of 0 to 60° C., preferably 20 to 30° C., and allyl is removed under the catalysis of a palladium catalyst or without a catalyst to obtain a compound represented by formula (I).

The above-mentioned halosuccinimide may be chlorosuccinimide, bromosuccinimide, iodosuccinimide or the like. The above-mentioned base may be sodium carbonate, potassium carbonate, sodium bicarbonate, cesium carbonate or the like. The above-mentioned inert gas may be nitrogen, argon or the like.

The intermediates and the target products obtained by the above-mentioned reactions can be isolated and refined by conventional refining methods commonly used in organic synthetic chemistry, such as filtration, extraction, washing, drying, concentration, recrystallization, various kinds of chromatography methods and the like according to needs. In addition, the intermediates may be also directly used in the next step without particular refining.

The resulting compounds of general formula (I) may also form an acid addition salt, a base addition salt, and various solvates such as hydrates in a conventional manner.

The various isomers can be separated by a conventional method taking advantage of differences in the physico-chemical properties between or among the isomers. For example, optically pure isomers can be isolated from a racemic mixture via a method wherein the racemic forms diastereomeric salts with a general optically active acid such as tartaric acid, or via a chromatography using optically active columns. In addition, the mixture of diastereomers can be resolved, for example, by separate crystallization or by various chromatographic methods. Further, optically active compounds may be also prepared using suitable optically active starting materials.

The present invention comprises the composition comprising one or more selected from the group consisting of the compound represented by formula (I), the pharmaceutically acceptable salts thereof, and the solvates thereof. The compositions may contain one or more pharmaceutically acceptable carriers. The aforesaid carriers are, for example, excipients and diluents, including water, lactose, glucose, fructose, sucrose, sorbitol, mannitol, polyethylene glycol, propylene glycol, starch, gum, gelatin, alginate, calcium silicate, calcium phosphate, cellulose, syrup, methyl cellulose, polyvinyl pyrrolidone, talc, magnesium stearate, stearic acid, glycerin, sesame oil, olive oil, soybean oil and other oils.

The present invention also comprises the pharmaceutical composition comprising any one of the compounds described above or a pharmaceutically acceptable salt or solvate thereof, with one or more uric acid-lowering agents, anti-gout agents, and anti-inflammatory agents. Said uric acid-lowering agent is selected from a group consisting of agents for reducing uric acid production and agents for promoting uric acid excretion. Said anti-inflammatory agents include immunomodulatory non-steroidal anti-inflammatory agents (NSAIDs) and glucocorticoids. The agent for reducing uric acid production is xanthine oxidase inhibitors selected from a group consisting of allopurinol, febuxostat, and pegloticase. Said agent for promoting uric acid excretion is urate anion transporter 1 (URAT1) inhibitors such as probenecid, benzbromarone, sulphinpyrazone and lesinurad. Said anti-gout agent is colchicine. Said non-steroidal anti-inflammatory agent is selected from a group consisting of non-selective non-steroidal anti-inflammatory agents and selective cyclooxygenase (COX-2) inhibitors. Said non-selective non-steroidal anti-inflammatory agents are selected from a group consisting of aspirin, benorilate, indomethacin, osaminethacine, sulindac, diclofenac sodium, ibuprofen, fenbid, ketoprofen, naproxen and piroxicam. Said selective cyclooxygenase (COX-2) inhibitor is selected from a group consisting of celecoxib, rofecoxib, parecoxib and so on. Said glucocorticoid is selected from a group consisting of dexamethasone, hydrocortisone, cortisone, prednisone, prednisolone, methylprednisolone, prednisone, prednisolone, and betamethasone.

The pharmaceutical composition of the present invention containing a compound represented by formula (I) or a pharmaceutically acceptable salt thereof or a solvate thereof as an effective ingredient may be orally administered, for example, in the form of tablets, capsules, granules, powders, syrups and the like, or administered by non-oral manners such as intravenous injection, intramuscular injection, sterile powder for injection, concentrated solution for injection, suppository, inhalant, transdermal absorbent, eye drops, and nose drops. In addition, when the pharmaceutical preparation of any of the above-described dosage forms is prepared by a conventional method, the active ingredient(s) may be used alone or in appropriate combination with other pharmaceutically acceptable carriers such as excipients, binders, extenders, disintegrants, surfactants, lubricants, dispersants, buffers, preservatives, flavoring agents, perfumes, coating agents, diluents, and the like.

The present invention also relates to a kit comprising the above-described composition, and an instruction containing one or more kinds of information selected from a group consisting of information indicating the disease state to which the the pharmaceutical composition is directed, storage information of the pharmaceutical composition, administration information and descriptions on how to administer the pharmaceutical composition.

The dose of the pharmaceutical composition of the present invention varies depending on the weight, age, gender, and symptom(s) of the patient, and can be appropriately selected depending on the way to administrate the composition such as oral administration or non-oral administration.

Hereinafter, the above-mentioned descriptions of the present invention will be explained in details by way of the specific embodiments in the form of examples. However, it should not be construed as limiting the scope of the above-described subject of the present invention to the following examples.

Example 1. Pharmacokinetics Experiment in Cynomolgus Monkeys (*Macaca fascicularis*)

The following test samples were used:
Compound A prepared by Preparation Example 2,
Compound B prepared by Preparation Example 1,
Compound C prepared by Preparation Example 3, and
Compound D prepared by Preparation Example 4.

The animal experiments were conducted in Peng-Li Biomedical Technology (Shanghai) Co., Ltd., and Shandong Hongli Medical Animal Experimental Research Co., Ltd.

The animals were purchased from Suzhou Xishan Zhongke Experimental Animal Co., Ltd.

Three non-naïve cynomolgus monkeys were administered with test compounds A, B and D at a dose of 5 mg/kg by intravenous injection and with test compound C at a dose of 3 mg/kg by intravenous injection, with one compound being tested at a time. Blood was collected from the vein before administration and 1 h, 3 h, 6 h and 24 h after administration, and plasma was isolated. The plasma was analyzed by a 4000 Q Trap LC-MS/MS instrument. The concentrations of the test samples were output by Analyst 1.6.1 from AB Company. The parameters ( ) such as the mean, standard deviation, and coefficient of variation were calculated using Microsoft Excel, wherein the values directly output by Analyst 1.6.1 requires no calculation. PK parameters were calculated using Pharsight Phoenix 6.2 software (NCA model).

Results of Half-life ($t_{1/2z}$ (h)) were shown in Table 1 below.

TABLE 1

$t_{1/2z}$ (h) (Mean ± SD) (n = 3) of compounds A, B, C and D administered in cynomolgus monkeys intravenously

| Group | $t_{1/2z}$ (h) |
|---|---|
| Compound A | 14.55 ± 6.69 |
| Compound B | 2.72 ± 0.35 |
| Compound C | 41.49 ± 12.31 |
| Compound D | 5.90 ± 0.42 |

It can be known from the experimental results that the half-life ($t_{1/2z}$(h)) values of compounds A, B, C and D administered in cynomolgus monkeys intravenously were significantly different among one another. The timing for sample collection in the uric acid-lowering experiment was designed according to the $t_{1/2z}$ (h).

Example 2. Uric acid-lowering experiment

The following test samples were used:
Compound A prepared by Preparation Example 2,
Compound B prepared by Preparation Example 1,
Compound C prepared by Preparation Example 3, and
Compound D prepared by Preparation Example 4;

The experiment was conducted by Peng-Li Biomedical Technology (Shanghai) Co., Ltd.

The animals were purchased from Suzhou Xishan Zhongke Experimental Animal Co., Ltd.

The experiment was done by reference to Komoriya K, Osada Y, Hasegawa M, Horiuchi H, Kondo S, Couch R C, Griffin T B. Hypouricemic effect of allopurinol and the novel xanthine oxidase inhibitor TEI-6720 in chimpanzees. Eur J Pharmacol. 1993 Dec. 21; 250(3): 455-60.

Each compound was tested in three non-naïve cynomolgus monkeys (1 #, 2 # and 3 #), wherein the monkeys were administered with test samples by intravenous injection. Blood was collected from the vein before administration and 1 h, 3 h, 6 h and 24 h after administration. The blood was left still at room temperature. The serum was collected by centrifugation. The content of uric acid in serum was measured.

Reduction rate of serum uric acid=(average uric acid content before administration−average uric acid content after administration)/average uric acid content before administration*100%.

Results were as follows. By reference to the half-life ($t_{1/2z}$ (h)) of compounds A, B, C and D administered in cynomolgus monkeys intravenously, the content of uric acid in serum and the reduction rate of serum uric acid before administration and 3 h and 6 h after administration of compound A, the content of uric acid in serum and the reduction rate of serum uric acid before administration and 3 h after administration of compound B, the content of uric acid in serum and the reduction rate of serum uric acid before administration and 24 h after administration of compound C, and the content of uric acid in serum and the reduction rate of serum uric acid before administration and 3 h after administration of compound D were determined, respectively. The specific results were shown in Tables 2 to 9 below.

TABLE 2

Test results of serum uric acid reduction by compound A

| Group | Content of serum uric acid (μmol/L) | | | |
|---|---|---|---|---|
| Animal No. | 1# | 2# | 3# | mean |
| Before administration | 75.9 | 91.9 | 63.7 | 77.2 |
| 3 h after administration | 61.9 | 57.0 | 59.9 | 59.6 |
| 6 h after administration | 67.6 | 47.6 | 50.4 | 55.2 |

TABLE 3

Reduction rate of serum uric acid by compound A

| Group | Reduction rate of serum uric acid (%) | | | |
|---|---|---|---|---|
| Animal No. | 1# | 2# | 3# | mean |
| Before administration | / | / | / | / |
| 3 h after administration | 18.5 | 38.0 | 5.98 | 22.8 |
| 6 h after administration | 10.9 | 48.2 | 20.9 | 28.5 |

TABLE 4

Test results of serum uric acid reduction by compound B

| Group | Content of serum uric acid (μmol/L) | | |
|---|---|---|---|
| Animal No. | 1# | 2# | mean |
| Before administration | 83.8 | 57.6 | 70.7 |
| 3 h after administration | 69.1 | 52.3 | 60.7 |

TABLE 5

Reduction rate of serum uric acid by compound B

| Group | Reduction rate of serum uric acid (%) | | |
|---|---|---|---|
| Animal No. | 1# | 2# | mean |
| Before administration | / | / | / |
| 3 h after administration | 17.5 | 9.2 | 14.1 |

TABLE 6

Test results of serum uric acid reduction by compound C

| Group | Content of serum uric acid (μmol/L) | | | |
|---|---|---|---|---|
| Animal No. | 1# | 2# | 3# | mean |
| Before administration | 57.5 | 64.9 | 58.9 | 60.4 |
| 24 h after administration | 45.8 | 38.3 | 50.7 | 44.9 |

TABLE 7

Reduction rate of serum uric acid by compound C

| Group | Reduction rate of serum uric acid (%) | | | |
|---|---|---|---|---|
| Animal No. | 1# | 2# | 3# | mean |
| Before administration | / | / | / | / |
| 24 h after administration | 20.3 | 41.0 | 13.9 | 25.7 |

TABLE 8

Test results of serum uric acid reduction by compound D

| Group | Content of serum uric acid (μmol/L) | | |
|---|---|---|---|
| Animal No. | 1# | 2# | mean |
| Before administration | 57.9 | 54.5 | 56.2 |
| 3 h after administration | 49.6 | 47.1 | 48.4 |

TABLE 9

Reduction rate of serum uric acid by compound D

| Group | Reduction rate of serum uric acid (%) | | |
|---|---|---|---|
| Animal No. | 1# | 2# | mean |
| Before administration | / | / | / |
| 3 h after administration | 14.3 | 13.6 | 13.9 |

It can be known from the test results that compounds A, B, C and D, can significantly reduce the serum uric acid levels in the test monkeys, as compared to the levels measured before administration, indicating that the compounds of formula (I) were effective in treating and/or preventing hyperuricemia, gout, gouty inflammations and uric acid nephropathy.

Example 3. Uric Acid-Lowering Test in Monkeys Having Hyperuricemia

The following test sample was used:
Compound A prepared by Preparation Example 2.

Glucose 5%, the solvent used in the example, was purchased from Chen Xin Pharmaceutical Co., Ltd., lot number 1312022142.

Uric acid (UA), a reagent used in the example, was purchased from Sigma-Aldrich Co., Ltd., lot number BCBM8832V.

The animal experiment was conducted by Shandong Hongli Medical Animal Experimental Research Co., Ltd.

The animals were purchased from Suzhou Xishan Zhongke Experimental Animal Co., Ltd.

The experiment was conducted by reference to Komoriya K, Osada Y, Hasegawa M, Horiuchi H, Kondo S, Couch R C, Griffin T B. Hypouricemic effect of allopurinol and the novel xanthine oxidase inhibitor TEI-6720 in chimpanzees. Eur J Pharmacol. 1993 Dec. 21; 250(3): 455-60.

In the Model group, three non-naïve cynomolgus monkeys (1 #, 2 # and 3 #) were administered with UA by subcutaneous injection at the nape. Blood was collected from the vein before UA administration and 0.5 h, 1 h, 2 h, 4 h, 6 h and 24 h after UA administration. The blood was left still at room temperature. The serum was collected by centrifugation. The content of serum uric acid was measured.

In the Administration group, three non-naïve cynomolgus monkeys (1 #, 2 # and 3 #) were administered with the test sample by intravenous injection after 2 weeks of clearance. Blood was collected from the vein before administration and 2 h after administration of test sample. Then, the monkeys were administered with UA by subcutaneous injection at the nape and blood was collected from the vein 1 h, 2 h and 4 h after the UA administration. The blood was left still at room temperature. The serum was collected by centrifugation. The content of serum uric acid was measured.

Reduction rate of serum uric acid in healthy monkeys administered with test sample=(average uric acid content before administration−average uric acid content 2 h after administration of test sample)/average uric acid content before administration*100%, Reduction rate of serum uric acid in monkeys having hyperuricemia after administration of test sample=(uric acid content after UA administration in the model group−uric acid content after UA administration in the administration group)/uric acid content in the model group*(100%).

The test results were as follows. By reference to the half-life (t½z 0.54 h) of uric acid (UA) in cynomolgus monkeys from the model group and also the trend in the change of the serum uric acid content, the timing for sample collection in the administration group were decided. That was, the samples were collected before administration, 2 h after administration of test sample and 1 h, 2 h and 4 h after UA administration for determination of the serum uric acid content. The contents of serum uric acid in the model group and the administration group and the reduction rates of serum uric acid were shown in the following Tables 3-1, 3-2 and 3-3, respectively.

TABLE 3-1

Test results of serum uric acid reduction in the Model group

| Group | Content of serum uric acid (μmol/L) | | | |
|---|---|---|---|---|
| Animal No. | 1# | 2# | 3# | mean |
| Before UA administration | 28.2 | 59.0 | 46.1 | 44.4 |
| 1 h after UA administration | 116.7 | 132.0 | 120.5 | 123.1 |
| 2 h after UA administration | 80.8 | 92.3 | 67.9 | 80.3 |
| 4 h after UA administration | 79.5 | 53.8 | 64.1 | 65.8 |

TABLE 3-2

Test results of serum uric acid reduction in the Administration group

| Group | Content of serum uric acid (μmol/L) | | | |
|---|---|---|---|---|
| Animal No. | 1# | 2# | 3# | mean |
| Before administration | 23.0 | 53.1 | 35.1 | 37.1 |
| 2 h after administration of test sample | 12.3 | 37.0 | 34.6 | 28.0 |
| 1 h after UA administration | 75.3 | 97.5 | 53.1 | 75.3 |
| 2 h after UA administration | 26.6 | 58.0 | 37.0 | 40.5 |
| 4 h after UA administration | 28.4 | 12.3 | 43.2 | 28.0 |

TABLE 3-3

Reduction rate of serum uric acid in the Administration group

| Group | Reduction rate or serum uric acid (%) | | | |
|---|---|---|---|---|
| Animal No. | 1# | 2# | 3# | mean |
| Before administration | / | / | / | / |
| 2 h after administration of test sample | 46.4 | 30.2 | 1.56 | 26.1 |
| 1 h after UA administration | 35.5 | 26.2 | 56.0 | 39.2 |
| 2 h alter UA administration | 67.1 | 37.2 | 45.5 | 49.1 |
| 4 h after UA administration | 64.3 | 77.1 | 32.6 | 58.0 |

It can be known from the test results that compound A can significantly reduce the content of serum uric acid in the test monkeys as compared to those in the model group (self-comparation), which indicated that compounds of formula (I) were useful in the treatment and/or prevention of hyperuricemia, gout, gouty inflammations, and uric acid nephropathy.

Example 4. Experiment on MSU-Induced Gouty Arthritis

The following test samples were used:
Compound A prepared by Preparation Example 2,
Compound B prepared by Preparation Example 1, and
Compound C prepared by Preparation Example 3.

Dimethyl sulfoxide, the solvent used in the example, was purchased from Sigma-Aldrich Co., Ltd., Lot number SZBD133SV.

Polyethylene glycol 15-hydroxystearate (Kolliphor HS 15), the solvent, was purchased from Beijing Feng-Li-Jing-Qiu Trade Co., Ltd., Lot number 19888216KO.

Glucose 5%, the solvent, was purchased from Chen Xin Pharmaceutical Co., Ltd., lot number 1312022142.

UA, a reagent used in the example, was purchased from Sigma-Aldrich Co., Ltd., lot number BCBM8832V.

Male Wistar rats were purchased from Beijing Weitong Lihua Experimental Animal Technology Co., Ltd.

The experiment was done by reference to Hsin-Pai Lee, Shi-Ying Huang, Yen-You Lin. Soft Coral-Derived Lemnalol Alleviates Monosodium Urate-Induced Gouty Arthritis in Rats by Inhibiting Leukocyte Infiltration and iNOS, COX-2 and c-Fos Protein Expression. March Agents 2013, 11, 99-113.

Preparation of MSU Crystal

One gram of uric acid was weighed, introduced into 200 mL of boiling water and heated. Then, NaOH (2 mol/L) was added until pH reached 9. The solution became clear, and was cooled at room temperature and then left still overnight. MSU was obtained after filtration, which was dried at 60° C. for 24 h and then sterilized at a high temperature of 180° C.

Male Wistar rats were raised for one week prior to the experiment and then randomly divided into groups. The toe volumes of the rats were measured one day prior to the experiment. The rats were administered with the solvent by subcutaneous injection in the model group at a dose of 5 mL/kg, while the rats were administered with test samples by subcutaneous injection in administration groups at a dose of 5 mg/kg. Rats were anesthetized immediately after administration and were injected with 0.09 mL of MSU suspension into the joint cavity of the left ankle. The volume of the left toe was measured in rats 9 h after the injection of MSU into the ankle joint cavity.

The test results were shown in Table 10 below.

TABLE 10

Results of gouty arthritis experiment (5 mg/kg)

| Group | Change of toe volume (mL) | Inhibition of toe volume change (%) |
|---|---|---|
| Model group | 0.504 | / |
| Group with compound A | 0.416 | 17.5 |
| Group with compound B | 0.349 | 30.8 |
| Group with compound C | 0.451 | 10.5 |

It can be known from the test results that compounds A, B and C could significantly inhibit the increase of the toe volumes in the test rats compared with the model group, which indicated that the compounds of formula (I) were useful in the treatment and/or prevention of hyperuricemia, gout, gouty inflammations, and uric acid nephropathy.

Example 5. Experiment on MSU-Induced Gouty Arthritis

The following test samples were used:
Compound A prepared by Preparation Example 2,
Compound C prepared by Preparation Example 3, and
Compound D prepared by Preparation Example 4.

Dimethyl sulfoxide, the solvent used in the example, was purchased from Sigma-Aldrich Co., Ltd., Lot number SZBD133SV.

Polyethylene glycol 15-hydroxystearate (Kolliphor HS 15), the solvent used in the example, was purchased from Beijing Feng-Li-Jing-Qiu Trade Co., Ltd., Lot number 19888216KO.

Glucose 5%, the solvent used in the example, was purchased from Chen Xin Pharmaceutical Co., Ltd., lot number 1312022142.

UA, a reagent used in the example, was purchased from Sigma-Aldrich Co., Ltd., lot number BCBM8832V.

Male Wistar rats were purchased from Beijing Weitong Lihua Experimental Animal Technology Co., Ltd.

The experiment was conducted by reference to Hsin-Pai Lee, Shi-Ying Huang, Yen-You Lin. Soft Coral-Derived Lemnalol Alleviates Monosodium Urate-Induced Gouty Arthritis in Rats by Inhibiting Leukocyte Infiltration and iNOS, COX-2 and c-Fos Protein Expression. March Agents 2013, 11, 99-113.

Preparation of MSU Crystal

One gram of uric acid was weighed, introduced into 200 mL of boiling water and heated. Then, NaOH (2 mol/L) was added until pH reached 9. The solution became clear, and was cooled at room temperature and then left still overnight. MSU was obtained after filtration, which was dried at 60° C. for 24 h and then sterilized at a high temperature of 180° C.

Male Wistar rats were raised for one week prior to the experiment and then randomly divided into groups. The toe volumes of the rats were measured one day prior to the experiment. The rats were administered with the solvent by subcutaneous injection in the model group at a dose of 15 mL/kg, while the rats were administered with test samples by subcutaneous injection in administration groups at a dose of 15 mg/kg or 10 mg/kg. Rats were anesthetized immediately after administration and were injected with 0.09 mL of MSU suspension into the joint cavity of the left ankle. The volume of the left toe was measured in rats 9 h after the injection of MSU into the ankle joint cavity.

The test results were shown in Table 11 below.

TABLE 11

Results of gouty arthritis experiment

| Group | Toe volume change (mL) | Inhibition of toe volume change (%) |
|---|---|---|
| Blank | −0.031 | / |
| Model group | 0.404 | / |
| Group with compound A (15 mg/kg) | 0.264 | 34.7 |
| Group with compound C (10 mg/kg) | 0.261 | 35.4 |
| Group with compound D (15 mg/kg) | 0.232 | 42.6 |

It can be known from the test results that compounds A, C and D could significantly inhibit the increase of the toe volumes in the test rats compared with the model group, which indicated that the compounds of formula (I) were useful in the treatment and/or prevention of hyperuricemia, gout, gouty inflammations, and uric acid nephropathy.

The rats with gouty arthritis were placed in a metabolic cage, and the palm center of the left foot of each rat was irritated with an electronic Von Frey pain threshold detector. The maximum stress value was recorded when each rat withdrew its foot, and the value was the pain value of that rat.

The test results were shown in Table 12 below.

TABLE 12

Pain values

| Group | Pain value (g) |
|---|---|
| Blank | 57.94 |
| Model group | 35.59 |
| Group with compound A (15 mg/kg) | 47.51 |
| Group with compound C (10 mg/kg) | 43.46 |
| Group with compound D (15 mg/kg) | 43.10 |

It can be known from the test results that compounds A, C and D could significantly increase the pain values in the test rats compared with the model group, which indicated that the compounds of formula (I) were useful in the treatment and/or prevention of hyperuricemia, gout, pain, gouty inflammations, and uric acid nephropathy.

Example 6. Experiment on MSU-Induced Gouty Arthritis Experiment

The following test sample was used:
Compound B prepared by Preparation Example 1.
Glucose 5%, a solvent used in the example, was purchased from Chen Xin Pharmaceutical Co., Ltd., lot number 1312022142.
UA, a reagent used in the example, was purchased from Sigma-Aldrich Co., Ltd., lot number BCBM8832V.
Male Wistar rats were purchased from Beijing Weitong Lihua Experimental Animal Technology Co., Ltd.
The experiment was conducted by reference to Hsin-Pai Lee, Shi-Ying Huang, Yen-You Lin. Soft Coral-Derived Lemnalol Alleviates Monosodium Urate-Induced Gouty Arthritis in Rats by Inhibiting Leukocyte Infiltration and iNOS, COX-2 and c-Fos Protein Expression. March Agents 2013, 11, 99-113.
Preparation of MSU Crystal
One gram of uric acid was weighed, introduced into 200 mL of boiling water and heated. Then, NaOH (2 mol/L) was added until pH reached 9. The solution became clear, and was cooled at room temperature and then left still overnight. MSU was obtained after filtration, which was dried at 60° C. for 24 h and then sterilized at a high temperature of 180° C.
Male Wistar rats were raised for one week prior to the experiment and then randomly divided into groups. The toe volumes of rats were measured one day prior to the experiment. The rats were administered with the solvent by subcutaneous injection in the model group at a dose of 15 mL/kg, while the rats were administered with the test sample by subcutaneous injection in administration group at a dose of 15 mg/kg. Rats were anesthetized immediately after administration and were injected with 0.09 mL of MSU suspension into the joint cavity of the left ankle. The volume of the left toe in each rat was measured 9 h after the injection of MSU into the ankle joint cavity.

The test results were shown in Table 13 below.

TABLE 13

Results of gouty arthritis experiment (15 mg/kg)

| Group | Toe volume change (mL) | Inhibition of toe volume change (%) |
|---|---|---|
| Blank | 0 | / |
| Model Group | 0.450 | / |
| Group with compound B | 0.229 | 49.1 |

It can be known from the test results that compound B could significantly inhibit the increase of the toe volumes in the test rats compared with the model group, which indicated that the compounds of formula (I) were useful in the treatment and/or prevention of hyperuricemia, gout, gouty inflammations, and uric acid nephropathy.

The rats with gouty arthritis were placed in a metabolic cage, and the palm center of the left foot of each rat was irritated with an electronic Von Frey pain threshold detector. The maximum stress value was recorded when each rat withdrew its foot, and the value was the pain value of that rat.

The test results were shown in Table 14 below.

TABLE 14

Pain values

| Group | Pain value (g) |
|---|---|
| Blank | 54.6 |
| Model group | 27.5 |
| Group with compound B | 37.2 |

It can be known from the test results that compound B could significantly reduce pain in the test rats compared with the model group, which indicated that the compound of formula (I) were useful in the treatment and/or prevention of hyperuricemia, gout, pain, gouty inflammations, and uric acid nephropathy.

Example 7. Experiment on LPS-Induced TNF-α Release

The following test samples were used:
Compound C prepared by Preparation Example 3, and
Compound D prepared by Preparation Example 4
Dimethyl sulfoxide, the solvent used in the example, was purchased from Sigma-Aldrich Co., Ltd., Lot number SZBD133SV.
Polyethylene glycol 15-hydroxystearate (Kolliphor HS 15), the solvent used in the example, was purchased from Beijing Feng-Li-Jing-Qiu Trade Co., Ltd., Lot number 19888216KO.
Glucose 5%, the solvent used in the example, was purchased from Chen Xin Pharmaceutical Co., Ltd., lot number 1312022142.
Lipopolysaccharide (LPS), a reagent used in the example, was available from Sigma-Aldrich Co., Ltd., Lot number 114M4009V.
Phosphate buffered saline (PBS), a reagent used in the example, was available from Life Technologies, Lot number 15552504.
Male BALB/C mice were purchased from Beijing Weitong Lihua Experimental Animal Technology Co., Ltd.
The experiment was conducted by reference to Pascale Gaillard, Isabelle Jeanclaude-Etter, etc. Design and Synthesis of the First Generation of Novel Potent, Selective, and in Vivo Active (Benzothiazol-2-yl)acetonitrile Inhibitors of the c-Jun N-Terminal. J. Med. Chem. 2005, 48, 4596-4607.

BALB/C mice were raised in the SPF-grade animal room for 1 week, and were then randomly divided into the corresponding model group and the administration groups according to the body weight. The rats were administered with the solvent or the test samples by subcutaneous injection at a dose of 10 mg/kg. The rats were administered with LPS by intraperitoneal injection at a dose of 15 mg/kg 30 min after the administration of the solvent or the test samples. The mice were anesthetized with sodium pentobarbital (45 mg/kg by intraperitoneal injection) 1 h after LPS administration. The blood was collected by cardiac puncture, and the content of TNF-α (tumor necrosis factor) in plasma was measured with a Mouse TNF-α Elisa Ready-set-go kit.

The test results were shown in Table 15 below.

TABLE 15

Results of LPS-induced INF-α release experiment

| Group | Content of TNF-α (pg/mL) | inhibition (%) |
|---|---|---|
| Model group | 1597 | / |
| Group with compound C | 1208 | 24.4 |
| Group with compound D | 1124 | 29.6 |

It can be known from the test results that compounds C and D could significantly reduce the content of TNF-α in the plasma of the test mice compared with the model group, which indicated that the compounds of formula (I) were useful in the treatment and/or prevention of gouty inflammations.

Example 8. Test on ConA-Induced IFNγ Release

The following test samples were used:
Compound A prepared by Preparation Example 2,
Compound C prepared by Preparation Example 3, and
Compound D prepared by Preparation Example 4.
Dimethyl sulfoxide, the solvent used in the example, was purchased from Sigma-Aldrich Co., Ltd., Lot number SZBD133SV.
Polyethylene glycol 15-hydroxystearate (Kolliphor HS 15), the solvent used in the example, was purchased from Beijing Feng-Li-Jing-Qiu Trade Co., Ltd., Lot number 19888216KO.
Glucose 5%, the solvent used in the example, was purchased from Chen Xin Pharmaceutical Co., Ltd., lot number 1312022142;
Concanavalin A (ConA), a reagent used in the example, was purchased from Sigma-Aldrich Co., Ltd., lot number SLBD7276V.
Dulbecco's Phosphate Buffered Saline (DPBS), a reagent used in the example, was purchased from Life Technologies, lot number 1627698.
Male C57BL/6 mice were purchased from Beijing Weitong Lihua Experimental Animal Technology Co., Ltd.
The experiment was conducted by reference to Dalya R. Soondl, Elisa Bjørgo, etc. PI3K p110δ regulates T cell cytokine production during primary and secondary immune responses in mice and humans. Blood. Author manuscript; available in PMC 2013 Mar. 11; and Gabriele Sass, Sonja Heinlein, etc. CYTOKINE EXPRESSION IN THREE MOUSE MODELS OF EXPERIMENTAL HEPATITIS. CYTOKINE, Vol. 19, No. 3 (7 Aug.), 2002: pp 115-120.

The C57BL/6 mice were raised in the SPF-grade animal room for 1 week, and were then randomly divided into the corresponding model group and the administration groups according to the body weight. The rats were administered with ConA by the tail vein injection at a dose of 15 mg/kg 30 min after the administration of the solvent or the test samples by subcutaneous injection at a dose of 20 mg/kg. After the mice were anesthetized with sodium pentobarbital (45 mg/kg by intraperitoneal injection) 3 h after administration of ConA, the blood was collected by cardiac puncture. The blood was placed in the centrifuge tube without anticoagulant and left still at room temperature. One hour later, the blood was centrifuged. The serum was extracted and stored at −80° C. The content of IFNγ (γ-interferon) in the serum was detected by a Mouse IFNγ Elisa Ready-set-go kit.

The test results were shown in Table 16 below.

TABLE 16

Results of ConA-iuduced IFNγ release test

| Group | Content of IFN-γ (pg/mL) | inhibition (%) |
|---|---|---|
| Model group | 3281 | / |
| Group with compound A | 2025 | 38.3 |
| Group with compound C | 2644 | 19.4 |
| Group with compound D | 2108 | 35.8 |

It can be known from the test results that compounds A, C and D could significantly reduce the content of IFNγ in the serum of the test mice compared with the model group, which indicated that the compounds of formula (I) were useful in the treatment and/or prevention of gouty inflammations.

Example 9. Experiment on Air Sacculitis

The following test sample was used:
Compound A prepared by Preparation Example 2.
Avicel RC-591, a solvent used in the example, was purchased from FMC BioPolymer, lot number DN14827450.
UA, a reagent used in the example, was purchased from Sigma-Aldrich.
Male SD rats were purchased from Shanghai Slack Experimental Animal Co., Ltd.
Experimental Method:
Preparation of MSU Suspension
One gram of uric acid was dissolved in 0.2 L of boiling water containing 6 mL of IN NaOH. The pH value was adjusted to 7.4. The solution was cooled at room temperature and stayed overnight at 4° C. The solution was then centrifuged, evaporated and dried to give MSU crystals. After the sonication treatment, the acicular crystals were found under the microscope to be 5-25 m in length. Five mg of the crystals were put into a glass flask, and then sterilized under a high pressure. The sterile MSU crystals were added to 5 mL of sterilized saline before injected into air sacs.
Male Wistar rats were raised for one week and then randomly divided into 6 groups. Animals were anesthetized and then injected with 24 mL of sterile air in their backs. The animals received the second injection of air 4 days later. On day 7, the rats in the blank group and model group were intragastrically administered with the solvent at a dose of 10 mL/kg; the rats in the dexamethasone group were administered by intraperitoneal injection with dexamethasone at a dose of 5 mg/kg; the rats in the colchicine group were intragastrically administered with colchicine at a dose of 5 mg/kg. In the high- and low-dose groups of compound A, the rats were intragastrically administered with compound A at the dose of 100 mg/kg and 30 mg/kg, respectively. One hour after administration, the rats in the blank group were injected with 5 mL of saline into the air sacs at the back, and the rats from other groups were injected with 5 mL of MSU crystal suspension (1 mg/mL) into the air sacs at the back. Four hours later, the lavage fluid in the air sacs was taken, and a portion of the lavage fluid was used for cytological analysis. The remaining was centrifuged at 8000 rpm for 15 min, and the supernatant was stored at −80° C. for the detection of cytokines IL-1β, IL-6, KC and TNFα. The test results were shown as mean±SEM and statistically analyzed by t-test.

The test results were shown in Tables 17 and 18 below.

dose of 100 mg/kg. This test demonstrated that compound A had a good anti-inflammatory effect in MSU-induced air sacs.

Example 10. Experiment on URAT1 (Urate Transporter 1)

The following test samples were used:
Compound A prepared by Preparation Example 2,
Compound B prepared by Preparation Example 1, and
Compound D prepared by Preparation Example 4.
Experimental Method:

The compounds were prepared into the stock solutions (5 mM) with dimethyl sulfoxide (DMSO). This experiment involved 8 concentrations in total. The final concentrations were 5000 nM, 1250 nM, 312.5 nM, 78.1 nM, 19.5 nM, 4.9 nM, 1.2 nM and 0.3 nM, respectively.

TABLE 17

Leukocyte counts(mean ± SEM, n = 8)

| Group | Total cell count(*$10^4$/air sacs) | Leukocyte count (*$10^4$/air sacs) | | | | |
|---|---|---|---|---|---|---|
| | | Monocyte | Lymphocyte | Eosinocyte | Basophil | Neutrophil |
| Blank group | 113.6 ± 20.9 | 106.2 ± 19.3 | 4.3 ± 1.3 | 0.9 ± 0.2 | 0 ± 0 | 2.1 ± 0.7 |
| Model group | 307.2 ± 74.2*** | 173 ± 31.3 | 11.1 ± 3.2 | 7.4 ± 2.7 | 0 ± 0 | 115.7 ± 77.2** |
| Dexamethasone group | 197.2 ± 22.8$$ | 171.0 ± 19.2 | 7.5 ± 1.1 | 4.8 ± 1.6 | 0 ± 0 | 13.8 ± 2.4$ |
| Colchicine group | 212.9 ± 28.8$ | 171.7 ± 20.1 | 12.1 ± 2.5 | 7.8 ± 2.0 | 0 ± 0 | 21.3 ± 6.6$ |
| Group with compound A at dose of 30 mg/kg | 206.8 ± 42.9$ | 174.2 ± 35.4 | 8.1 ± 1.2 | 5.8 ± 1.2 | 0 ± 0 | 18.6 ± 6.4$ |
| Group with compound A at dose of 100 mg/kg | 176.2 ± 29.6$$$ | 151.4 ± 24.1 | 8.0 ± 1.9 | 4.6 ± 1.4 | 0 ± 0 | 12.2 ± 3.4$ |

Note:
**$P < 0.01$,
***$P < 0.001$, in comparison with the blank group;
$$P < 0.05$,
$$$P < 0.01$,
$$$$P < 0.001$, in comparison with the model group.

TABLE 18

Cytokines (mean ± SEM, n = 8)

| Group | IL-1β (pg/mL) | IL-16 (pg/mL) | KC (pg/mL) | TNF-α (pg/mL) |
|---|---|---|---|---|
| Blank group | 44.1 ± 5.1 | 257.9 ± 37.3 | 3745.8 ± 281.8 | 12.0 ± 1.7 |
| Model group | 98.1 ± 28.2* | 4287.4 ± 3362.4*** | 15776.3 ± 6515.9*** | 40.5 ± 9.4*** |
| Dexamethasone group | 27.8 ± 3.9$$$ | 136.4 ± 44.2$$ | 1653.5 ± 364.8$$$ | 6.6 ± 1.2$$$ |
| Colchicine group | 112.6 ± 16.2 | 1132.0 ± 281.4 | 9892.7 ± 2046.2 | 32.2 ± 5.3 |
| Group with compound A at dose of 30 mg/kg | 79.2 ± 15.5 | 1218.2 ± 498.7 | 8742.1 ± 1151.3 | 29.7 ± 5.0 |
| Group with compound A at dose of 100 mg/kg | 88.6 ± 13.8 | 476.6 ± 140.6$ | 5757.4 ± 554.5$ | 18.7 ± 1.6$$ |

Note:
*$P < 0.05$,
***$P < 0.001$, in comparison with the blank group:
$$P < 0.05$,
$$$P < 0.001$,
$$$$P < 0.001$, in comparison with the model group.

The test results showed that dexamethasone and colchicine can significantly inhibit the increase of the total cell count and neutrophil count in the lavage fluid caused by MSU. Compound A could significantly inhibit the increase of the total cell count and neutrophil count in the lavage fluid at the oral doses of 30 mg/kg and 100 mg/kg. Dexamethasone could significantly inhibit the increase of IL-1β, IL-6, KC and TNFα caused by MSU. Compound A could significantly inhibit the increase of IL-6, KC and TNFα at the oral 2. Preparation of buffers: chlorine-free HBSS buffer (125 mM sodium gluconate, 4.8 mM potassium gluconate, 1.3 mM calcium gluconate, 1.2 mM $KH_2PO_4$, 1.2 mM $MgSO_4$, 5.6 mM glucose, 25 mM 4-hydroxyethylpiperazine ethanesulfonic acid (HEPES) (pH 7.4)); lysis buffer (100 mM NaOH)

3. Transfected cells stably expressing human urate transporter 1 (hURAT1) were obtained by: placing human embryonic kidney cells (HEK-293T) in a cell culture plate containing complete medium, incubating the cells for 24 h at 37° C. in 5% $CO_2$, rinsing the cells with phosphate buffered saline (PBS) followed by trypsin digestion to prepare a suspension containing single cells; placing $8\times10^6$ cells a cell culture plate, adding dropwise TransIT-293 Reagent:DNA complexes (1.5 ml of Opti-MEM I Reduced-Serum Medium, 15 g of plasmid DNA, and 45 μL of TransIT-293 Reagent were mixed uniformly and then incubated at room temperature for 30 min) to different areas of the cell culture plate, gently shaking the cell culture plate to homogeneously distribute the TransIT-293 Reagent:DNA complexes, and incubating the cells for 48 h at 37° C. in 5% $CO_2$.

4. Uptake of $^{14}C$-labeled uric acid in hURAT1 transfected cells: (1) hURAT1-transfected cells were placed in a Poly-D-lysine 96-well microplate at a cell density of $6\times10^4$/well, and left still overnight at 37° C. in 5% $CO_2$; (2) after the cells were placed in the Poly-D-lysine 96-well microplate for 12 h, the cells were washed for 3 times with 200 μl of pre-heated chlorine-free HBSS buffer per well, and the washing solution in the microplate was removed; (3) 50 μl of uric acid-containing [8-14C] (0.1 μCi/well) chlorine-free HBSS buffer was added per well, and then 5 μl of the test compound was added per well and incubated for 5 min at 37° C.; (4) the incubation buffer was removed and the uptake of uric acid [8-14C] was stopped by adding 100 μl of ice-cold, chlorine-free HBSS buffer; (5) the plate was washed for 3 times with the chlorine-free HBSS buffer and the buffer was cleared from the wells; (6) 50 μl of the lysis buffer was added per well, and the plate was subject to shaking at 600 rpm for 10 min; (7) the microplate was placed in a centrifuge, and then centrifuged at 1000 rpm for 5 min, and 45 μl of the supernatant was taken into an Isoplate-96 Microplate; 8) 150 μl of Ultima Gold™ XR scintillation cocktail was added per well, and the plate was shaken for 10 min at 600 rpm; the Isoplate-96 microplate was placed in MicroBeta Trilux (PerkinElmer) to measure the radiation intensity of $^{14}C$.

5. Calculation of $IC_{50}$ Value

Inhibition rate (%)=(signal intensity of the positive control−signal intensity of the compound)/(signal intensity of the positive control−signal intensity of the negative control)×100

GraphPad Prism 5.0 was used for the analysis to obtain $IC_{50}$ values.

The test results were shown in Table 19.

TABLE 19

Inhibition of hURATI activity by compounds of the present invention

| Test samples | $IC_{50}$ (μM) |
|---|---|
| Compound A | 2.52 |
| lesinurad* | >5 |
| Compound B | 3.02 |
| Compound D | 0.87 |

Lesinurad*, which compound was a new agent developed by AstraZeneca approved by FDA in December of 2015 for the treatment of gout, with a chemical name of 2-[[5-bromo-4-(4-cyclopropyl-1-naphthyl)-4H-1,2,4-triazol-3-yl]thio] acetic acid.

From Table 19, it was known that the compound of the present invention had a good inhibitory effect on hURAT1 (human urate transporter 1).

Preparation Example 1

Preparation of 8-chloro-3-butyl-3,7-dihydro-1H-purine-2,6-dione (Compound B)

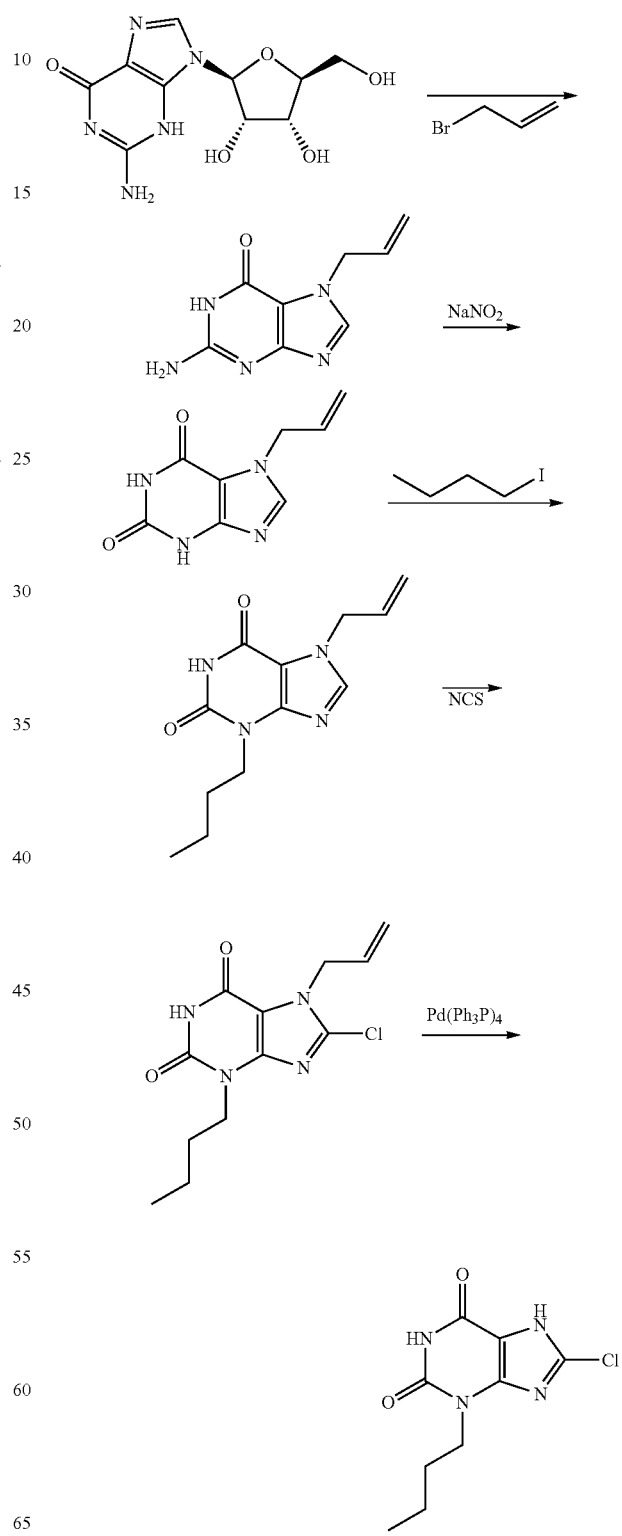

(1) Preparation of 7-allyl-2-amino-1H-purine-6-(7H)-one

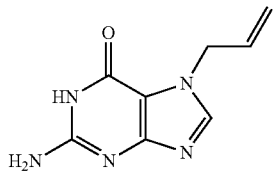

Guanosine (2000 g, 7.07 mol) and allyl bromide (1950.5 g, 16.20 mol) were dissolved in DMSO (100 mL) and stirred for 18 h at room temperature under nitrogen protection. Concentrated hydrochloric acid (37%, 5 L) was added to the solution, followed by stirring for 1 h. The solution was added with 2 L of methanol and then neutralized with 2 N solution of sodium hydroxide until solids were precipitated. The solids were filtered out, and the filter cake was dried in an oven to give a white solid (1210 g, yield: 89.6%).

(2) Preparation of 7-allyl-1H-purine-2,6-(3H, 7H)-dione

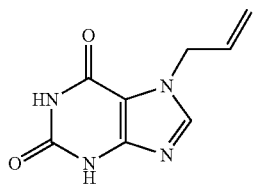

The 7-allyl-2-amino-1H-purine-6 (7H)-one (1200 g, 6.28 mol) was dissolved in acetic acid (3 L) and water (750 mL). An aqueous solution (600 mL) of sodium nitrite (1732 g, 25.1 mol) was added dropwise to the aforesaid system. The mixture was stirred for 3 h with reaction proceeding. The solution was concentrated to one third and left still to precipitate solids. The solids were filtered out, and the filter cake was dried to give a light yellow solid (875 g, yield: 72.8%).

(3) Preparation of 7-allyl-3-butyl-1H-purine-2,6-(3H, 7H)-dione

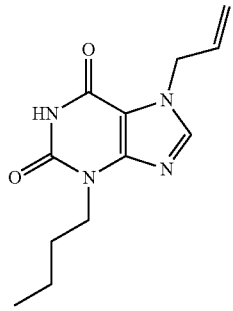 [SMILES: C=CCn1cnc2c1c(=O)[nH]c(=O)n2CCCC]

The 7-allyl-1H-purine-2,6-(3H, 7H)-dione (400 g, 2.08 mol), iodo-n-butane (422 g, 2.29 mol) and potassium carbonate (345 g, 2.50 mol) were dissolved in anhydrous DMF (1.6 L). The mixture was stirred for 24 h with reaction proceeding. Ethyl acetate (2 L) and diluted hydrochloric acid (2 N, 500 mL) were added. Then, extraction was performed. The organic phase was dried by rotary evaporation to give a light yellow solid (185 g, yield: 35.9%).

(4) Preparation of 7-allyl-3-butyl-8-chloro-1H-purine-2,6-(3H, 7H)-dione

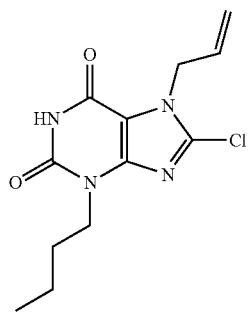 [SMILES: C=CCn1c(Cl)nc2c1c(=O)[nH]c(=O)n2CCCC]

The 7-allyl-3-butyl-1H-purine-2,6-(3H, 7H)-dione (160 g, 0.645 mol) was dissolved in anhydrous DMF (800 mL), and NCS (94.7 g, 0.71 mol) was added thereto. The reaction mixture was stirred under nitrogen protection for 24 h, and then subjected to rotary evaporation. Ethyl acetate (200 mL) was added for recrystallization. The crystals were filtered out, and the filter cake was dried to give a light yellow solid (110.2 g, yield: 60.5%).

(5) Preparation of 8-chloro-3-butyl-3,7-dihydro-1H-purine-2,6-dione

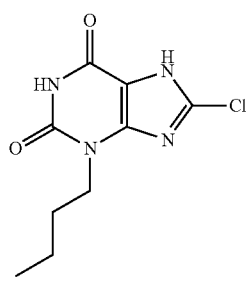 [SMILES: CCCCn1c(=O)[nH]c(=O)c2[nH]c(Cl)nc21]

The crude 7-allyl-3-butyl-8-chloro-1H-purine-2,6-(3H, 7H)-dione (565 mg, 2.0 mmol), tetrakistriphenylphosphine palladium (104 mg, 0.09 mmol) and morpholine (775 mg, 8.9 mmol) were dissolved in 20 mL of dichloromethane. The reaction was performed for 12 h at room temperature under nitrogen protection. Then, the solution was concentrated and subjected to column chromatography using silica gel columns (petroleum ether:ethyl acetate=1:1) to give a light yellow solid (80 mg, yield: 16.5%).

Molecular formula: $C_9H_{11}ClN_4O_2$; molecular weight: 242.1; mass spectrum (M+H): 243.0

$^1$H-NMR (DMSO-$d_6$, 400 MHz): 0.85 (t, 3H), 1.23-1.27 (m, 2H), 1.54-1.59 (m, 2H), 3.81 (t, 2H), 11.17 (s, 1H), 14.25 (br.s, 1H).

Preparation Example 2

Preparation of 8-chloro-3-pentyl-3,7-dihydro-1H-purine-2,6-dione (Compound A)

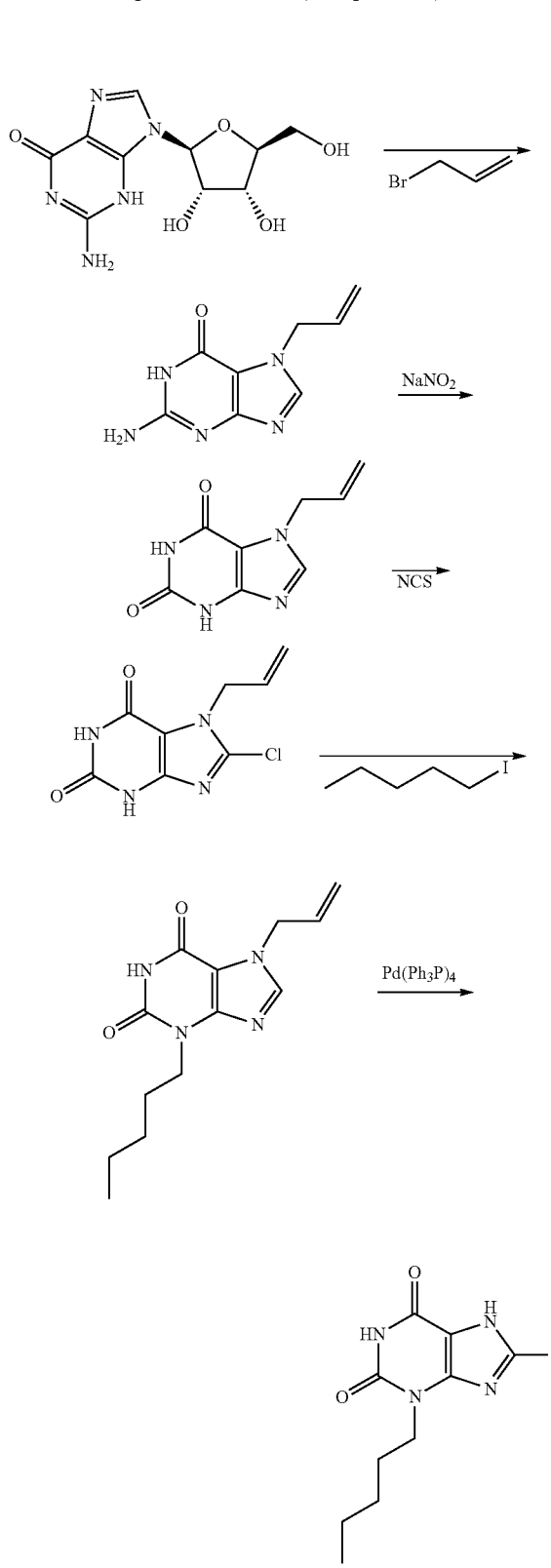

Preparation of 7-allyl-2-amino-1H-purine-6(7H)-one

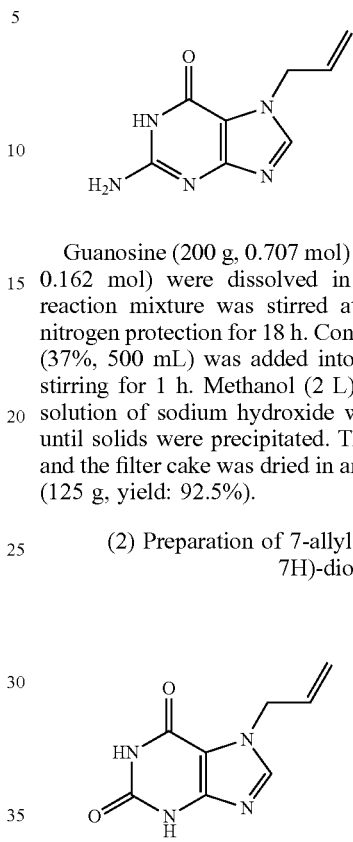

Guanosine (200 g, 0.707 mol) and allyl bromide (19.51 g, 0.162 mol) were dissolved in DMSO (1000 mL). The reaction mixture was stirred at room temperature under nitrogen protection for 18 h. Concentrated hydrochloric acid (37%, 500 mL) was added into the solution, followed by stirring for 1 h. Methanol (2 L) was added, and then 2 N solution of sodium hydroxide was used for neutralization until solids were precipitated. The solids were filtered out, and the filter cake was dried in an oven to give a white solid (125 g, yield: 92.5%).

(2) Preparation of 7-allyl-1H-purine-2,6-(3H, 7H)-dione

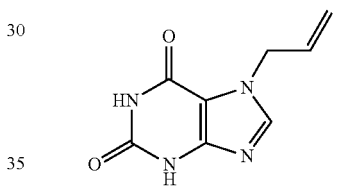

The 7-allyl-2-amino-1H-purine-6-(7H)-one (120 g, 0.628 mol) was dissolved in acetic acid (1.5 L) and water (150 mL). An aqueous solution (300 mL) of sodium nitrite (173.2 g, 2.51 mol) was added dropwise to the above system. The reaction mixture was stirred for 3 h. The reaction solution was concentrated to one third, and left still to precipitate solids. The solids were filtered out, and the filter cake was dried to give a light yellow solid (85 g, yield: 70.5%).

(3) Preparation of 7-allyl-8-chloro-1H-purine-2,6-(3H, 7H)-dione

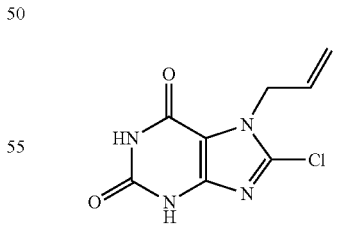

The 7-allyl-1H-purine-2,6-(3H, 7H)-dione (2.10 g, 10.9 mmol) was dissolved in anhydrous DMF (12 mL), and N-chlorosuccinimide (1.60 g, 12.0 mmol) was added thereto. The reaction mixture was stirred for 6 h under nitrogen protection. The reaction system was poured into water, extracted with ethyl acetate and then subjected to rotary evaporation to give a crude light yellow solid of 1.20 g.

(4) Preparation of 7-allyl-3-pentyl-8-chloro-1H-purine-2,6-(3H, 7H)-dione

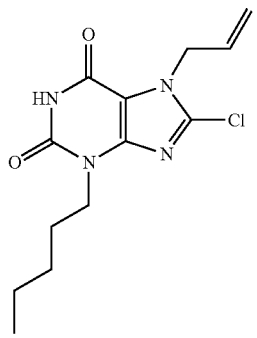 [SMILES: C=CCn1c(Cl)nc2c1c(=O)[nH]c(=O)n2CCCCC]

The crude 7-allyl-8-chloro-1H-purine-2,6-(3H, 7H)-dione (750 mg) and sodium carbonate (383 mg, 3.61 mmol) were dissolved in anhydrous DMF (10 mL), and iodo-n-pentane (690 mg, 3.48 mmol) was added thereto. The reaction mixture was stirred for 24 h. The reaction system was poured into water. Ethyl acetate (100 mL) and dilute hydrochloric acid (2N, 50 mL) were added. The extraction was then performed. The organic phase was dried by rotary evaporation to give a crude light yellow oil of 500 mg.

(5) Preparation of 8-chloro-3-pentyl-3,7-dihydro-1H-purine-2,6-dione

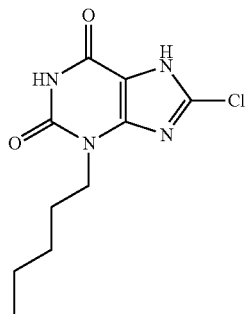 [SMILES: CCCCCn1c(=O)[nH]c(=O)c2[nH]c(Cl)nc21]

The target compound was prepared (80 mg, yield: 4.6%) by the method described in step (5) of Example 1.

Molecular formula: $C_{10}H_{13}ClN_4O_2$; molecular weight: 256.1; mass spectrum (M+H): 257.1

$^1$H-NMR (DMSO-$d_6$, 600 MHz): 0.83 (t, 3H), 1.19-1.29 (m, 4H), 1.57-1.60 (m, 2H), 3.84 (t, 2H), 11.19 (s, 1H), 14.38 (br.s, 1H).

Preparation Example 3

Preparation of 8-chloro-1-methyl-3-butyl-3,7-dihydro-1H-purine-2,6-dione (Compound C)

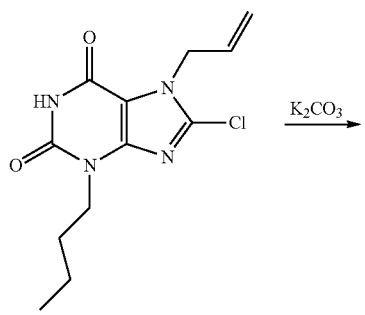

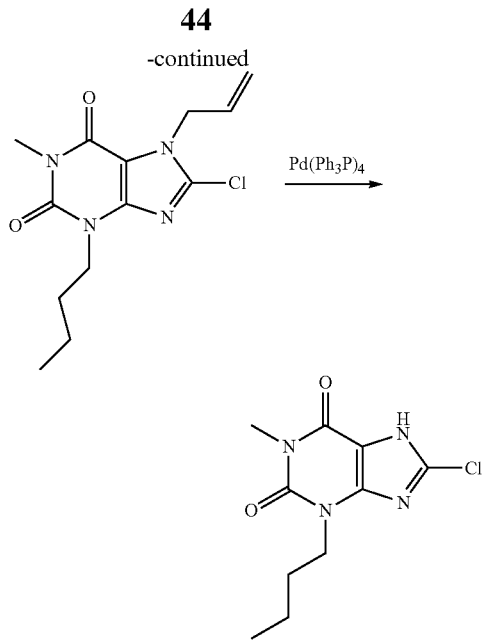

Preparation of 8-chloro-1-methyl-3-butyl-7-(2-propen-1-yl)-1H-purine-2,6-(3H, 7H)-dione

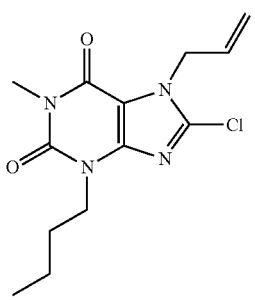 [SMILES: C=CCn1c(Cl)nc2c1c(=O)n(C)c(=O)n2CCCC]

8-chloro-3-butyl-7-(2-propen-1-yl)-1H-purine-2,6-(3H, 7H)-dione (565 mg, 2.0 mmol) and potassium carbonate (304 mg, 2.2 mmol) were added into N,N-dimethylformamide (15 mL), and then iodomethane (341 mg, 2.4 mmol) was added thereto. The reaction was performed at 80° C. for 12 h. The resultant was dissolved in ethyl acetate, and then washed with 2 N dilute hydrochloric acid and a saturated solution of sodium chloride once in said order. The solution was dried and concentrated to give a crude brown product of 400 mg.

(2) Preparation of 8-chloro-1-methyl-3-butyl-3,7-dihydro-1H-purine-2,6-dione

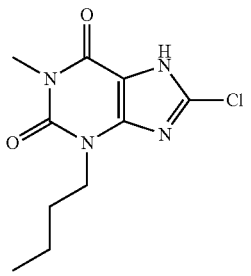 [SMILES: CCCCn1c(=O)n(C)c(=O)c2[nH]c(Cl)nc21]

The crude 8-chloro-1-methyl-3-butyl-7-(2-propen-1-yl)-1H-purine-2,6-(3H, 7H)-dione (400 mg), tetrakistriphenylphosphine palladium (104 mg, 0.09 mmol) and morpholine (775 mg, 8.9 mmol) were dissolved in 20 mL of dichloromethane. The reaction was performed for 12 h at room temperature under nitrogen protection. Then, the resultant was concentrated and subjected to column chromatography using silica gel columns (petroleum ether:ethyl acetate=2:1) to give a light yellow solid of 112 mg. The yield in the two steps was 23.1%.

Molecular formula: $C_{10}H_{13}ClN_4O_2$; molecular weight: 256.1; mass spectrum (M+H): 257.0

$^1$H-NMR (DMSO-$d_6$, 400 MHz) 0.88 (t, 3H), 1.27-1.32 (m, 2H), 1.60-1.65 (m, 2H), 3.23 (s, 3H), 3.92 (t, 2H), 14.45 (s, 1H).

Preparation Example 4

Preparation of 8-chloro-1-methyl-3-pentyl-3,7-dihydro-1H-purine-2,6-dione (Compound D)

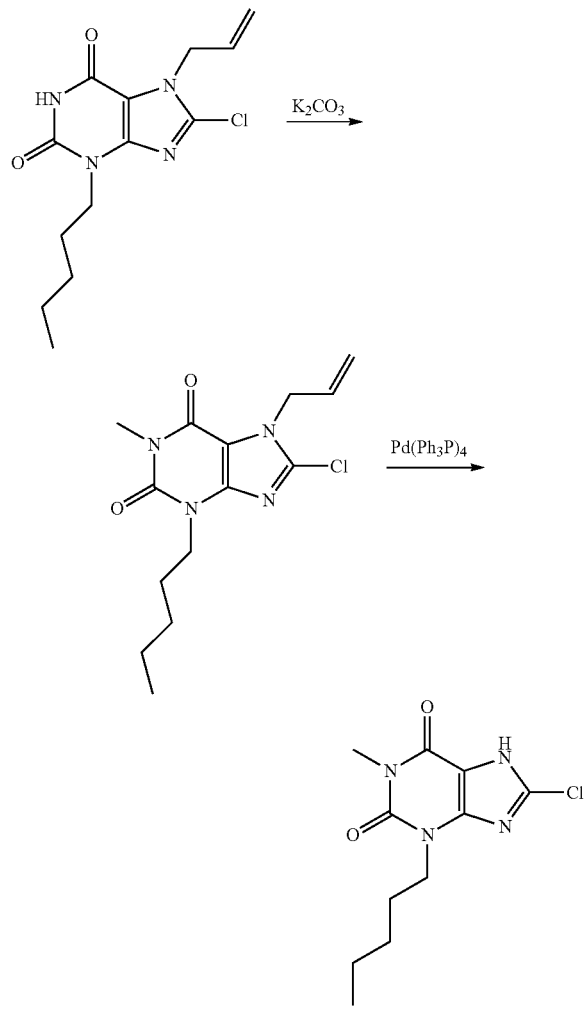

The target compound of 120 mg, with a yield in two steps being 26.3%, was prepared by the method described in Examples 1-3.

Molecular formula: $C_{11}H_{15}ClN_4O_2$; molecular weight: 270.1; mass spectrum (M+H): 271.1

$^1$H-NMR (DMSO-$d_6$, 400 MHz) 0.86 (t, 3H), 1.25-1.33 (m, 4H), 1.62-1.67 (m, 2H), 3.23 (s, 3H), 3.92 (t, 2H), 14.45 (br.s, 1H).

Preparation Example 5

Preparation of 8-chloro-3-(3-methylbutyl)-3,7-dihydro-1H-purine-2,6-dione (Compound E)

The target compound was prepared by the method described in Examples 1-3.

$^1$H-NMR (DMSO-$d_6$, 400 MHz) 0.90 (d, 6H), 1.47-1.62 (m, 3H), 3.86 (t, 2H), 11.18 (br.s, 1H), 14.38 (br.s, 1H).

Preparation Example 6

Preparation of 8-chloro-3-(2-cyclopropylethyl)-3,7-dihydro-1H-purine-2,6-dione (Compound F)

The target compound was prepared by the method described in Examples 1-3.

$^1$H-NMR (DMSO-$d_6$, 400 MHz) 0.00-0.06 (m, 2H), 0.36-0.42 (m, 2H), 0.67-0.77 (m, 1H), 1.60 (q, 2H), 4.06-4.10 (m, 2H).

Preparation Example 7

Preparation of 8-chloro-3-pentyl-3,7-dihydro-1H-purine-2,6-dione monohydrate

Preparation of 7-allyl-2-amino-1H-purine-6 (7H)-one

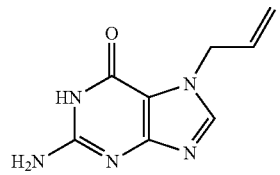

Guanosine (4000 g, 14.1 mol) and allyl bromide (3900 g, 32.2 mol) were dissolved in DMSO (11 L). The solution was stirred for 24 h at room temperature. Concentrated hydrochloric acid (37%, 7500 mL) was added to the solution, followed by stirring for 1 h. The solution was added with methanol (20 L) and then neutralized with saturated solution of sodium hydroxide until solids were precipitated. The solids were filtered out and washed with water, and the filter cake was dried in an oven to give a white solid (1585 g, yield: 58.7%).

(2) Preparation of 7-allyl-1H-purine-2,6-(3H, 7H)-dione

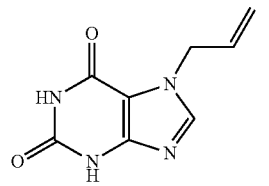

The 7-allyl-2-amino-1H-purine-6 (7H)-one (1584 g, 8.29 mol) was dissolved in acetic acid (8.5 L) and water (1500 mL). An aqueous solution of sodium nitrite (2277 g, 33 mol) was added dropwise to the aforesaid system. The reaction mixture was stirred overnight. Solids were filtered out and washed with water. The filter cake was dried to give a white solid (1086 g, yield: 68.2%).

(3) Preparation of 7-allyl-8-chloro-1H-purine-2,6-(3H, 7H)-dione

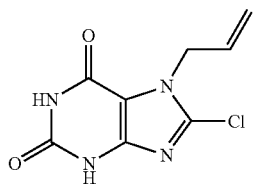

The 7-allyl-1H-purine-2,6-(3H, 7H)-dione (2166.3 g, 11.3 mmol) was dissolved in anhydrous DMF (8 L), and N-chlorosuccinimide (1657 g, 12.4 mmol) was added thereto. The reaction mixture was stirred for 24 h under nitrogen protection. EA was added, and the solution was cooled and subjected to suction filtration. The solids filtered out was washed with EA and then dried to give a white solid (1804 g, yield: 70.6%).

(4) Preparation of 7-allyl-3-pentyl-8-chloro-1H-purine-2,6-(3H, 7H)-dione

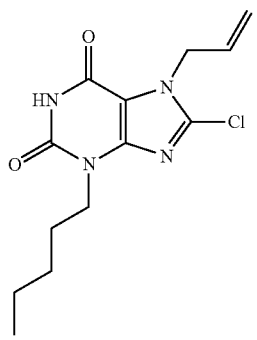 [SMILES: C=CCn1c(Cl)nc2c1c(=O)[nH]c(=O)n2CCCCC]

The 7-allyl-8-chloro-1H-purine-2,6-(3H, 7H)-dione (200 g, 0.88 mol) was dissolved in anhydrous DMF (1.2 L). Sodium carbonate (116.6 g, 1.1 mol) was added, and then iodo-n-pentane (173 g, 0.87 mol) was also added. The reaction mixture was stirred for 4 days. The reaction system was poured into water, and solids were precipitated. Suction filtration was performed. The obtained solids were washed with n-hexane. The solids were subjected to suction filtration again and dried to give a white solid (197 g, yield: 75.2%).

(5) Preparation of 8-chloro-3-pentyl-3,7-dihydro-1H-purine-2,6-dione monohydrate

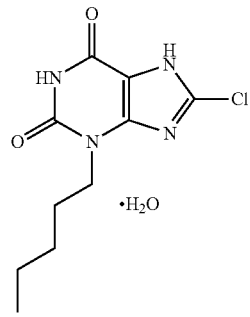

The 7-allyl-3-pentyl-8-chloro-1H-purine-2,6-(3H, 7H)-dione (96 g, 0.32 mol), tetrakistriphenylphosphine palladium (13 g, 0.011 mmol) and N,N-dimethylbarbituric acid (253 g, 1.62 mol) were dissolved in 1 L of dichloromethane. The reaction was performed for 12 h at room temperature under nitrogen protection, and suction filtration was then carried out. The obtained solids were dissolved in an aqueous solution of sodium hydroxide, and then washed with dichloromethane. The pH of aqueous phase was adjusted to 4 by using dilute HCl. Solids were precipitated. Suction filtration was performed. The obtained solids were dried to give a white solid (60 g, yield: 67.7%).

Molecular formula: $C_{10}H_{15}ClN_4O_3$; molecular weight: 274.1; mass spectrum (M+H): 257.1

$^1$H-NMR (DMSO-$d_6$, 400 MHz): 0.84-0.86 (t, 3H), 1.28 (m, 4H), 1.63 (m, 2H), 3.85 (t, 2H), 11.22 (s, 1H), 14.38 (br.s, 1H).

What is claimed is:

1. A method for reducing uric acid level comprising administering a compound represented by formula (I), or a pharmaceutically acceptable salt thereof or a solvate thereof to a mammal in need thereof,

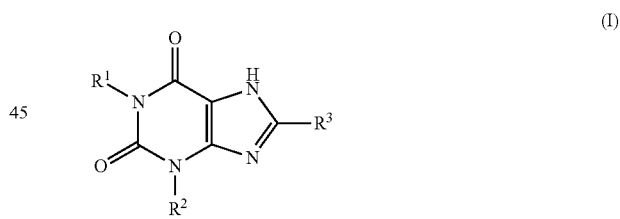

wherein
R$^1$ is hydrogen or C$_{1-4}$ alkyl, wherein said C$_{1-4}$ alkyl is unsubstituted or substituted with one or more of halogen, cyano, CF$_3$ or a combination thereof;
R$^2$ is selected from the group consisting of C$_{1-10}$ alkyl, C$_{2-6}$ alkenyl and C$_{2-6}$ alkynyl, wherein said C$_{1-10}$ alkyl, C$_{2-6}$ alkenyl or C$_{2-6}$ alkynyl is unsubstituted or substituted with halogen or cyano, or a combination thereof; and
R$^3$ is halogen or cyano.

2. The method of claim 1, wherein,
R$^1$ represents hydrogen or methyl,
R$^2$ represents ethyl, propyl, 2-methylpropyl, butyl, 3-methylbutyl or pentyl, and
R$^3$ represents fluorine or chlorine.

3. The method of claim 1, wherein the compound is selected from the group consisting of:

8-chloro-3-pentyl-3,7-dihydro-1H-purine-2,6-dione,
8-chloro-3-butyl-3,7-dihydro-1H-purine-2,6-dione,
8-chloro-1-methyl-3-butyl-3,7-dihydro-1H-purine-2,6-dione,
8-chloro-1-methyl-3-pentyl-3,7-dihydro-1H-purine-2,6-dione,
8-chloro-3-(3-methylbutyl)-3,7-dihydro-1H-purine-2,6-dione,
8-chloro-3-(2-methylpropyl)-3,7-dihydro-1H-purine-2,6-dione, and
8-chloro-1-methyl-3-(3-methylbutyl)-3,7-dihydro-1H-purine-2,6-dione.

4. The method of claim 1, wherein the solvate of the compound is a hydrate.

5. The method of claim 2, wherein the solvate of the compound is a hydrate.

6. The method of claim 3, wherein the solvate of the compound is a hydrate.

7. The method of claim 1, wherein the compound is 8-chloro-3-pentyl-3,7-dihydro-1H-purine-2,6-dione, or a hydrate thereof.

8. The method of claim 1, wherein the method for reducing uric acid level is used to prevent or treat uratic disease or gouty disease.

9. The method of claim 8, wherein the uratic disease or the gouty disease is hyperuricemia, gout, gouty inflammation, gouty pain or uric acid nephropathy.

10. The method of claim 9, wherein the hyperuricemia is primary hyperuricemia or secondary hyperuricemia.

11. The method of claim 9, wherein the gout is primary gout or secondary gout.

12. The method of claim 9, wherein the gouty inflammation is acute gouty arthritis, subcutaneous tophi, or chronic tophi arthritis.

13. The method of claim 9, wherein the uric acid nephropathy is acute uric acid nephropathy, chronic urate nephropathy or uric acid urolithiasis.

14. A method for reducing uric acid level comprising administering a pharmaceutical composition comprising one or more selected from the group consisting of a compound represented by formula (I), a pharmaceutically acceptable salt thereof and a solvate thereof, and one or more pharmaceutically acceptable carriers to a mammal in need thereof,

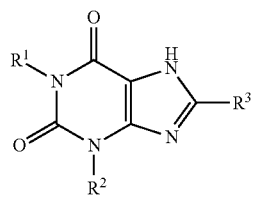

(I)

wherein $R^1$ is hydrogen or $C_{1-4}$ alkyl, wherein said $C_{1-4}$ alkyl is unsubstituted or substituted with one or more of halogen, cyano, $CF_3$ or a combination thereof;

$R^2$ is selected from the group consisting of $C_{1-10}$ alkyl, $C_{2-6}$ alkenyl and $C_{2-6}$ alkynyl, wherein said $C_{1-10}$ alkyl, $C_{2-6}$ alkenyl or $C_{2-6}$ alkynyl is unsubstituted or substituted with halogen or cyano, or a combination thereof; and $R^3$ is halogen or cyano.

15. The method of claim 14, wherein, $R^1$ represents hydrogen or methyl, $R^2$ represents ethyl, propyl, 2-methylpropyl, butyl, 3-methylbutyl or pentyl, and $R^3$ represents fluorine or chlorine.

16. The method of claim 14, wherein the compound is selected from the group consisting of:

8-chloro-3-pentyl-3,7-dihydro-1H-purine-2,6-dione,
8-chloro-3-butyl-3,7-dihydro-1H-purine-2,6-dione,
8-chloro-1-methyl-3-butyl-3,7-dihydro-1H-purine-2,6-dione,
8-chloro-1-methyl-3-pentyl-3,7-dihydro-1H-purine-2,6-dione,
8-chloro-3-(3-methylbutyl)-3,7-dihydro-1H-purine-2,6-dione,
8-chloro-3-(2-methylpropyl)-3,7-dihydro-1H-purine-2,6-dione, and
8-chloro-1-methyl-3-(3-methylbutyl)-3,7-dihydro-1H-purine-2,6-dione.

17. The method of claim 14, wherein the solvate of the compound is a hydrate.

18. The method of claim 14, wherein the method for reducing uric acid level is used to prevent or treat uratic disease or gouty disease.

19. The method of claim 18, wherein the uratic disease or the gouty disease is hyperuricemia, gout, gouty inflammation, gouty pain or uric acid nephropathy.

20. The method of claim 19, wherein the hyperuricemia is primary hyperuricemia or secondary hyperuricemia; the gout is primary gout or secondary gout; the gouty inflammation is acute gouty arthritis, subcutaneous tophi, or chronic tophi arthritis; and the uric acid nephropathy is acute uric acid nephropathy, chronic urate nephropathy or uric acid urolithiasis.

* * * * *